United States Patent
Hoffman et al.

(10) Patent No.: US 8,047,430 B2
(45) Date of Patent: *Nov. 1, 2011

(54) ACCOUNT ADMINISTRATION PLANS AND SYSTEMS

(75) Inventors: Glen A. Hoffman, Conway, AR (US); Jason Lee, Cabot, AR (US); John J. Robbins, Jr., Little Rock, AR (US); Clayton Hall, Conway, AR (US); John J. Robbins, Sr., Little Rock, AR (US)

(73) Assignee: DataPath, Inc., Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,808

(22) Filed: Dec. 20, 2010

(65) Prior Publication Data

US 2011/0106705 A1     May 5, 2011

Related U.S. Application Data

(63) Continuation of application No. 11/337,390, filed on Jan. 23, 2006, now Pat. No. 7,857,205.

(51) Int. Cl.
*G07F 19/00*     (2006.01)
(52) U.S. Cl. .................................................. 235/379
(58) Field of Classification Search .......... 235/379, 235/381; 705/2

See application file for complete search history.

(56) References Cited

U.S. PATENT DOCUMENTS

| 7,213,750 B1 | 5/2007 | Barnes et al. |
| 7,661,586 B2 | 2/2010 | Robbins, Jr. et al. |
| 2001/0037214 A1 | 11/2001 | Raskin et al. |
| 2002/0035529 A1 | 3/2002 | Tooke |
| 2005/0261968 A1 | 11/2005 | Randall et al. |
| 2006/0113376 A1 | 6/2006 | Reed et al. |
| 2006/0212313 A1 | 9/2006 | Hoffman et al. |
| 2006/0212378 A1 | 9/2006 | Hoffman et al. |
| 2010/0145848 A1 | 6/2010 | Robbins, Jr. et al. |

OTHER PUBLICATIONS

Crock, H.V., "Anterior Lumbar Interbody Fusion Indications for its Use and Notes on Surgical Technique," *Clinical Orthopedics*; vol. 165; pp. 157-163; May 1982.

Wilterberger, B.R., Abbott, K.H., "Dowel Intervertebral Fusion as Used in Lumbar Disc Surgery," *The Journal of Bone and Joint Surgery*, vol. 39A, cover page and pp. 284-292, and 331, 1957.

*Primary Examiner* — Seung Lee

(57) ABSTRACT

A computer system for facilitating payments from an account according to particular embodiments of the invention is adapted for: (1) facilitating the transmission, to a plan service provider, of a first set of documentation of a first payment that would potentially qualify for reimbursement from the account; (2) receiving, from the plan service provider, verification that the first payment has been verified as qualifying for reimbursement from the account according to a set of reimbursement rules associated with the account; (3) storing, in memory, an electronic version of the first set of documentation; and (4) storing, in memory, an indication that the first payment has been verified as being properly reimbursable from the account.

19 Claims, 19 Drawing Sheets

ACCOUNT ADMINISTRATION PLANS AND SYSTEMS

CROSS-REFERENCE TO RELATED APPLICATIONS

This application is a continuation application of U.S. patent application Ser. No. 11/337,390, filed Jan. 23, 2006, entitled "Account Administration Plans and Systems," which claims priority to U.S. Provisional Patent Application No. 60/645,864, entitled "Account Administration Plans and Systems," filed on Jan. 21, 2005, the entire contents of which applications are incorporated herein by reference.

BACKGROUND OF THE INVENTION

Currently, it is common practice for an "Eligible Individual" as defined by Section 223 of the Internal Revenue Code ("Code") to have, on deposit with a custodian or trustee, funds maintained as a Health Savings Account ("HSA"). As defined by Section 223 of the Code, an Eligible Individual is a person who: (1) is covered by a qualified High Deductible Health Plan ("HDHP"); (2) is not receiving benefits under Medicare; (3) is not covered by any non-HDHP; and (4) is not claimed as a dependent by any taxpayer other than the individual's spouse.

It is current practice for individuals to administer HSA's on their own. Accordingly, individuals typically establish an HSA directly with a financial institution that will serve as the Custodian or Trustee (herein collectively referred to as the "custodian") of their HSA funds. Similarly, once an HSA has been set up, the individual holding the HSA (the "account holder") typically works directly with the custodian of their HSA to administer the account. Accordingly, it is currently the account holder's responsibility to assure that the HSA is being properly administered. This can be difficult and time consuming for the account holder.

In light of the above, there is currently a need for systems and methods for facilitating the administration of HSA's, while assuring that HSA account holders comply with the applicable laws.

SUMMARY OF THE INVENTION

A method of facilitating payments from a health savings account according to various embodiments of the invention comprises the steps of: (A) receiving a first set of documentation of a first payment that would potentially qualify for reimbursement from a health savings account, the health savings account being associated with an account holder; (B) after receiving the first set of documentation, using the first set of documentation to verify that the first payment qualifies for reimbursement from the health savings account; and (C) after verifying that the first payment qualifies for reimbursement from the health savings account: (1) storing, in a computer system, an electronic version of the first set of documentation; and (2) storing, in the computer system, an indication that the first payment has been verified as being properly reimbursable from the health savings account.

A computer system for facilitating payments from an account according to particular embodiments of the invention is adapted for: (1) facilitating the transmission, to a plan service provider, of a first set of documentation of a first payment that would potentially qualify for reimbursement from the account; (2) receiving, from the plan service provider, verification that the first payment has been verified as qualifying for reimbursement from the account according to a set of reimbursement rules associated with the account; (3) storing, in memory, an electronic version of the first set of documentation; and (4) storing, in memory, an indication that the first payment has been verified as being properly reimbursable from the account.

BRIEF DESCRIPTION OF THE DRAWINGS

Figure 1:
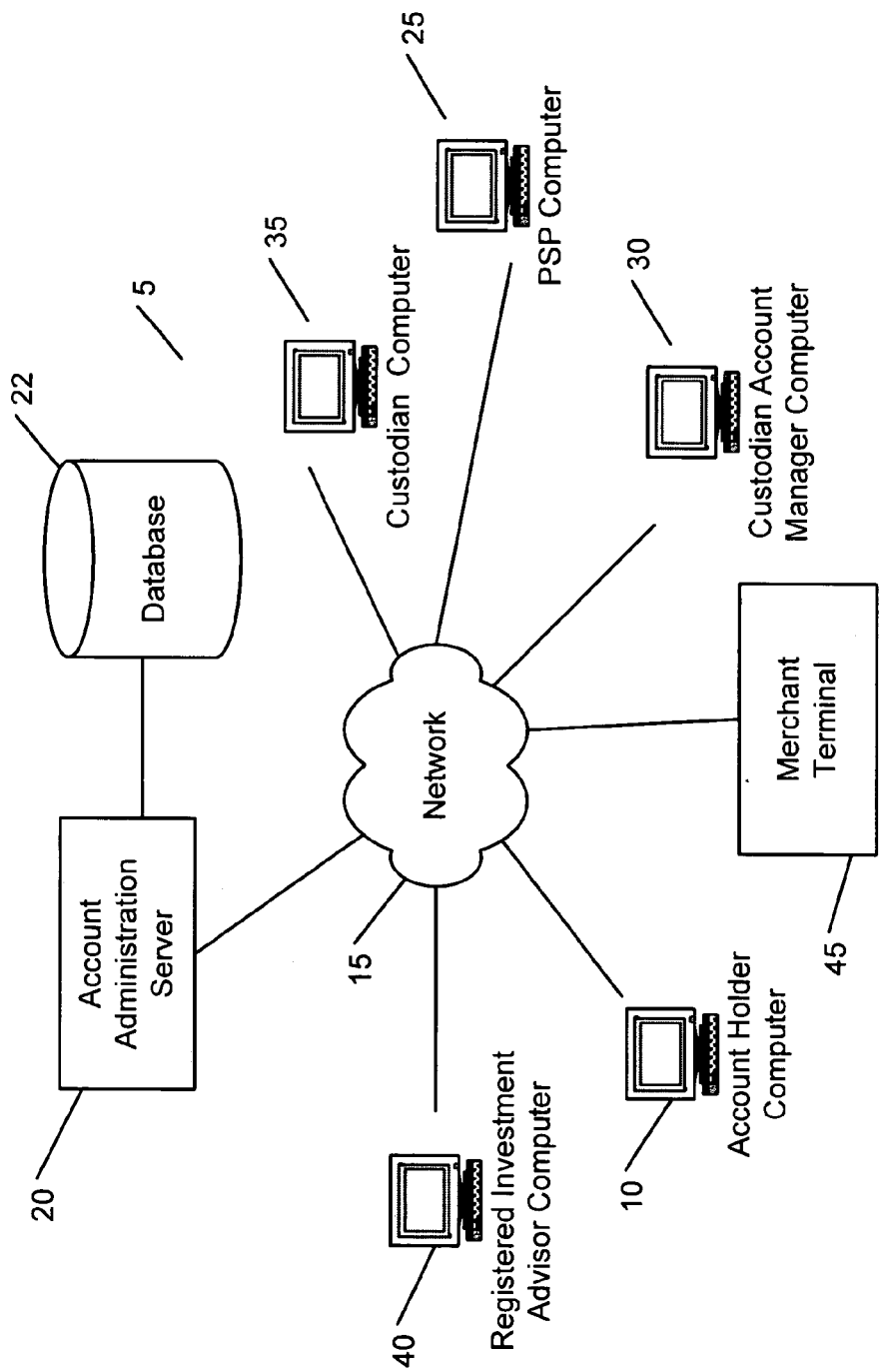

Having thus described the invention in general terms, reference will now be made to the accompanying drawings, which are not necessarily drawn to scale, and wherein:

FIG. 1 is a block diagram of an account administration system according to a particular embodiment of the invention.

Figure 2:
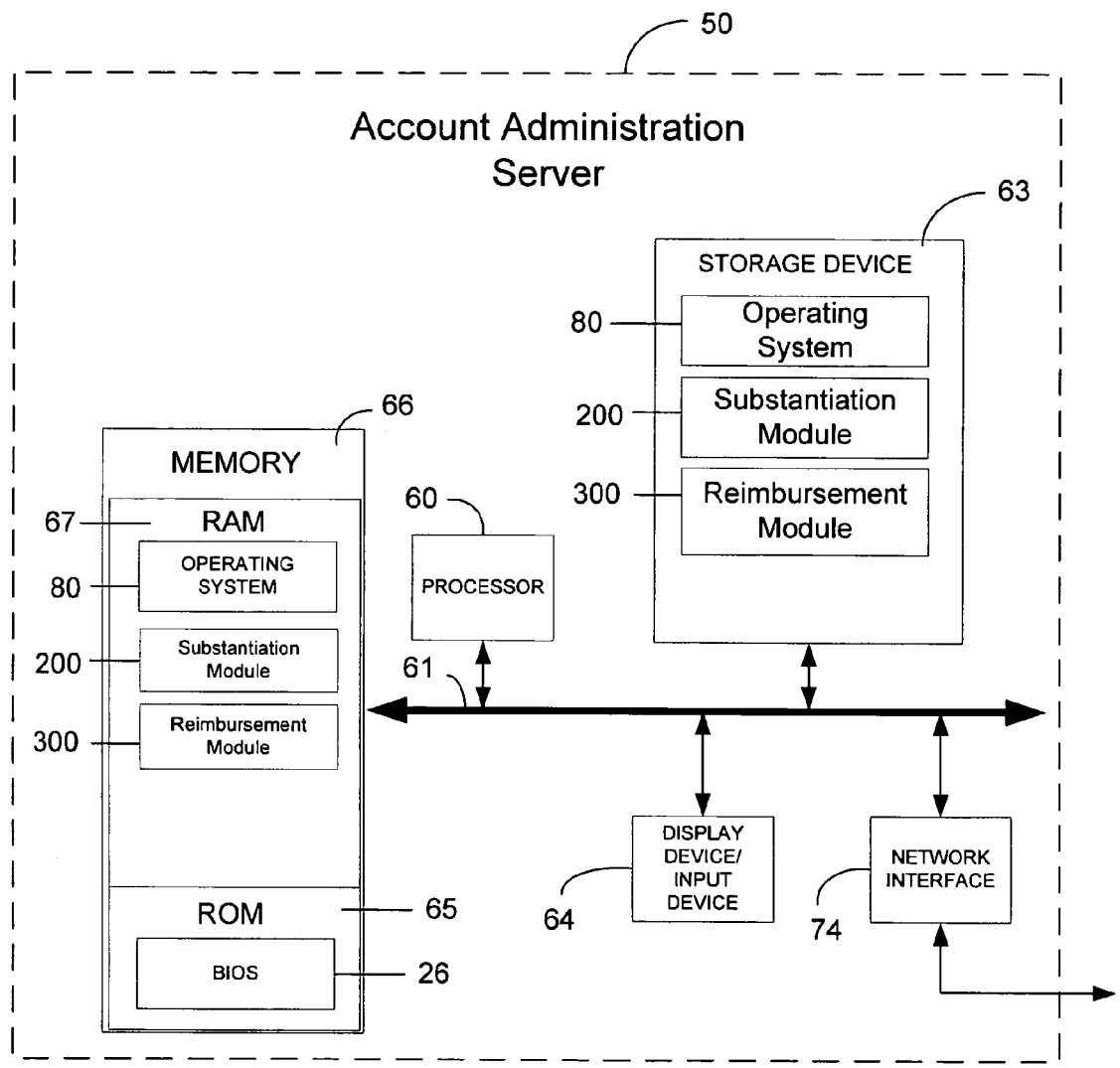

FIG. 2 is a diagram of an Account Administration Server according to one embodiment of the invention.

Figure 3:
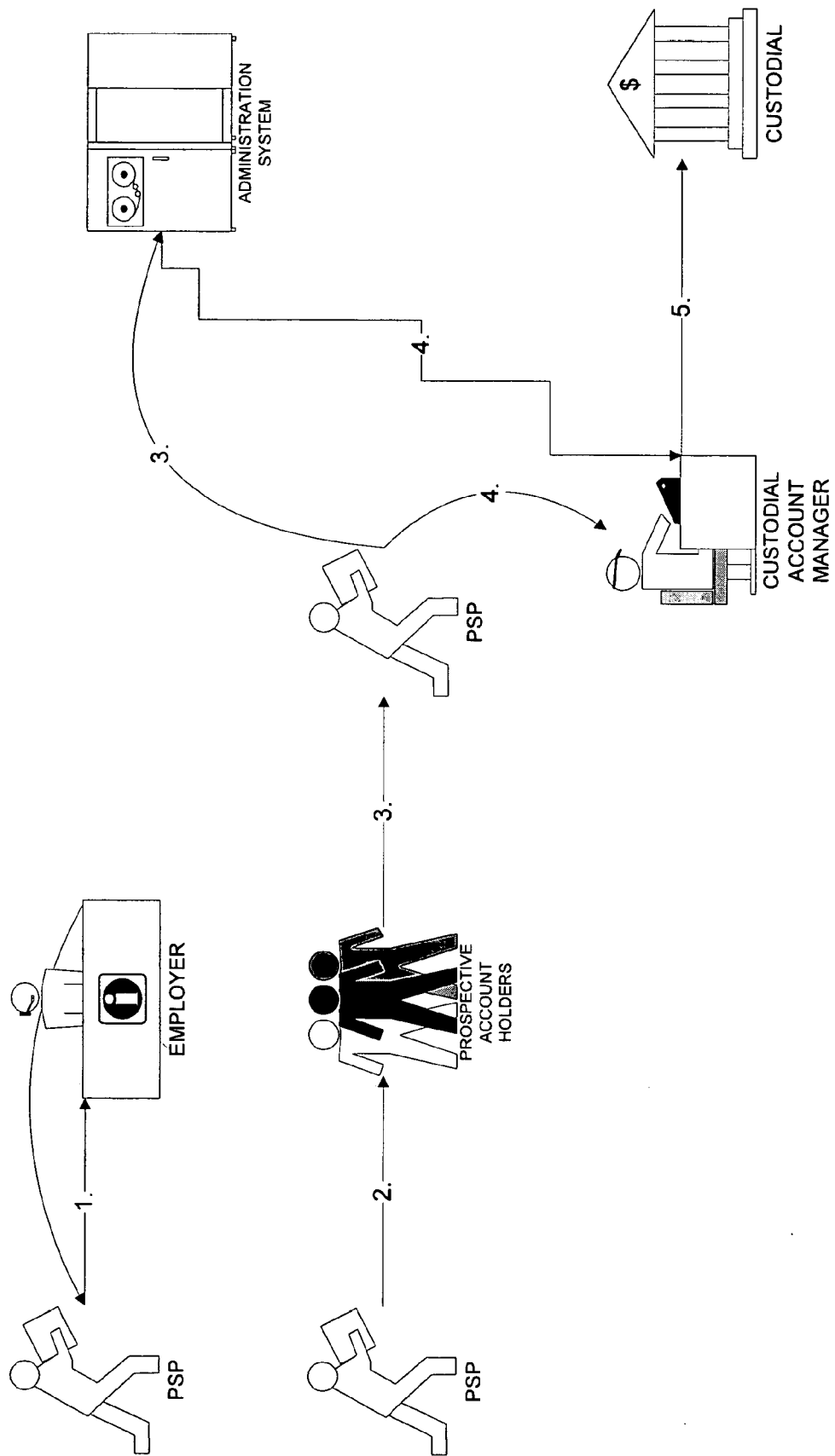

FIG. 3 is a diagram that visually illustrates various steps taken, in various embodiments of the invention, during the process of establishing an account.

Figure 4:
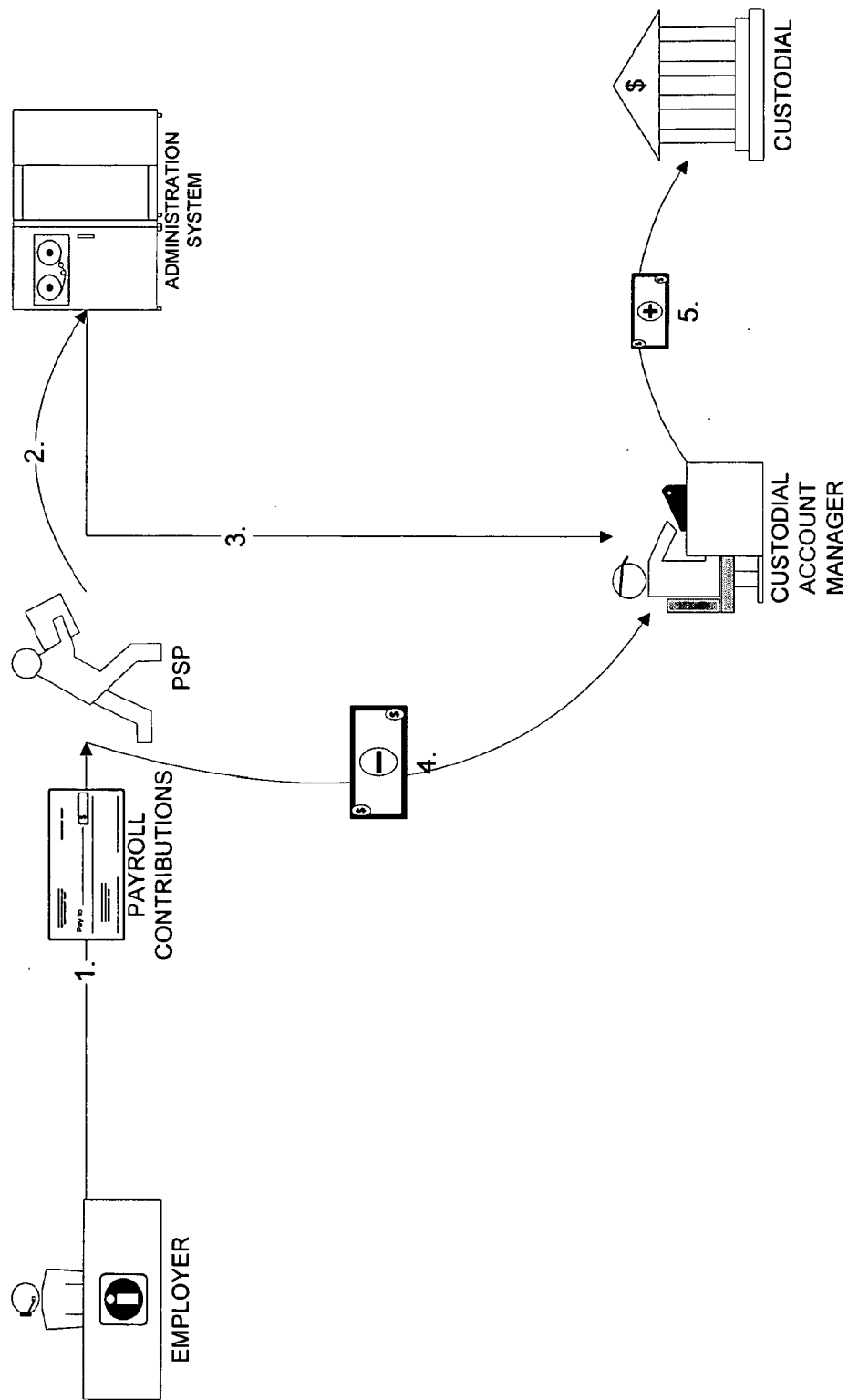

FIG. 4 is a diagram that visually illustrates various steps taken, in various embodiments of the invention, during the process of making contributions to an account.

Figure 5:
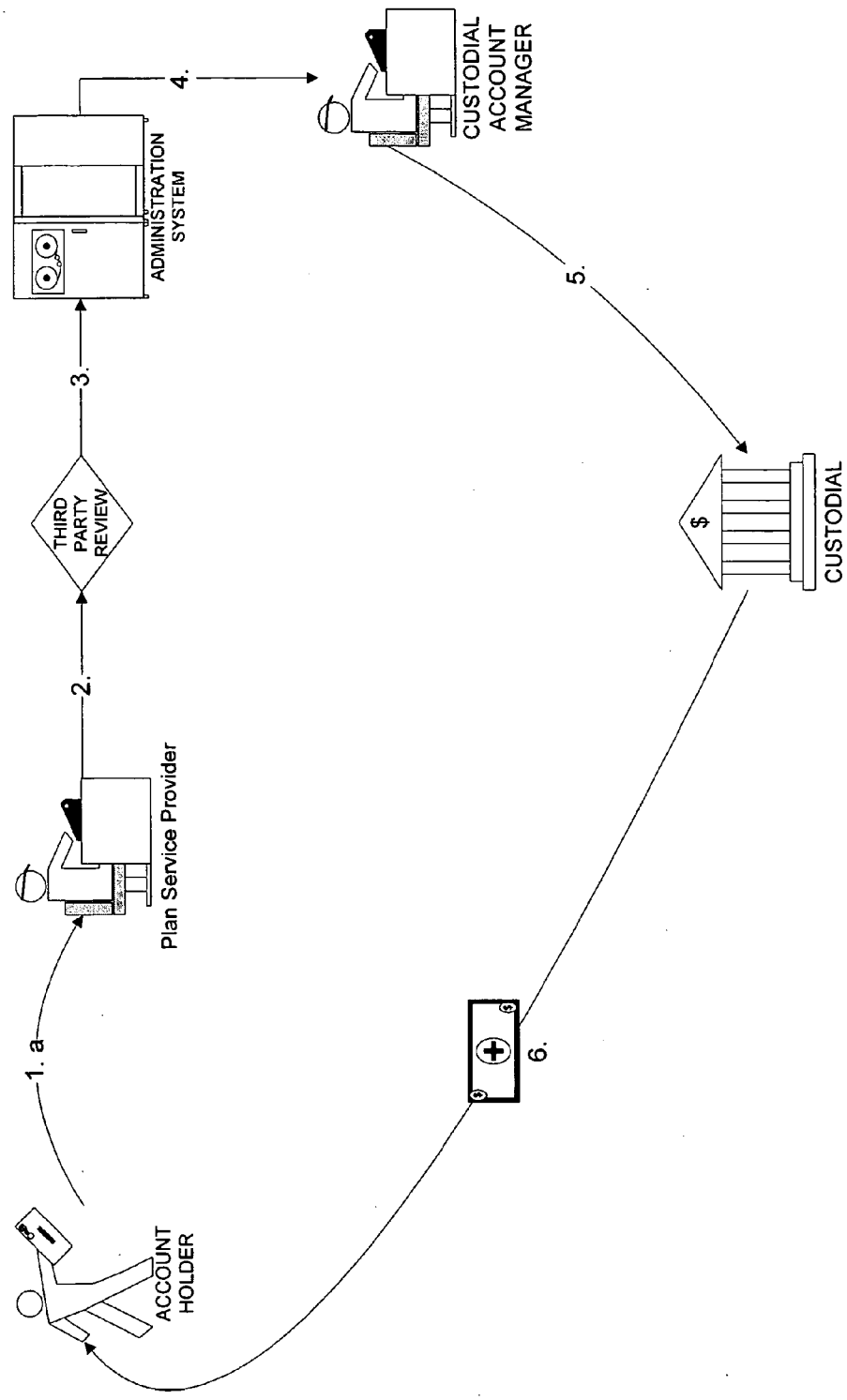

FIG. 5 is a diagram that visually illustrates various steps taken, in various embodiments of the invention, during the process of making distributions from an account.

Figure 6:
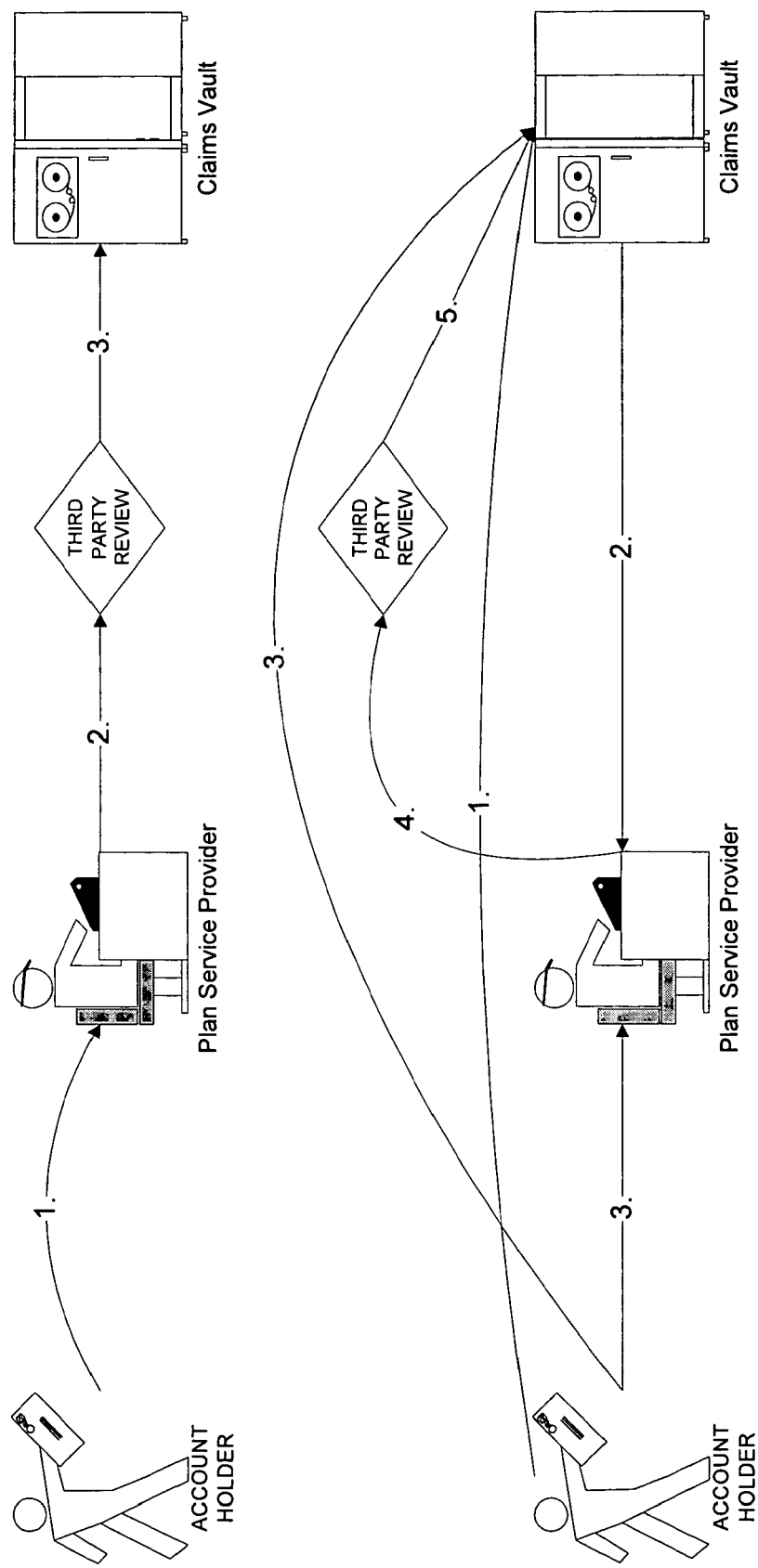

FIG. 6 is a diagram that visually illustrates various steps taken, in various embodiments of the invention, during the process of storing a claim a "claims vault".

Figure 7:
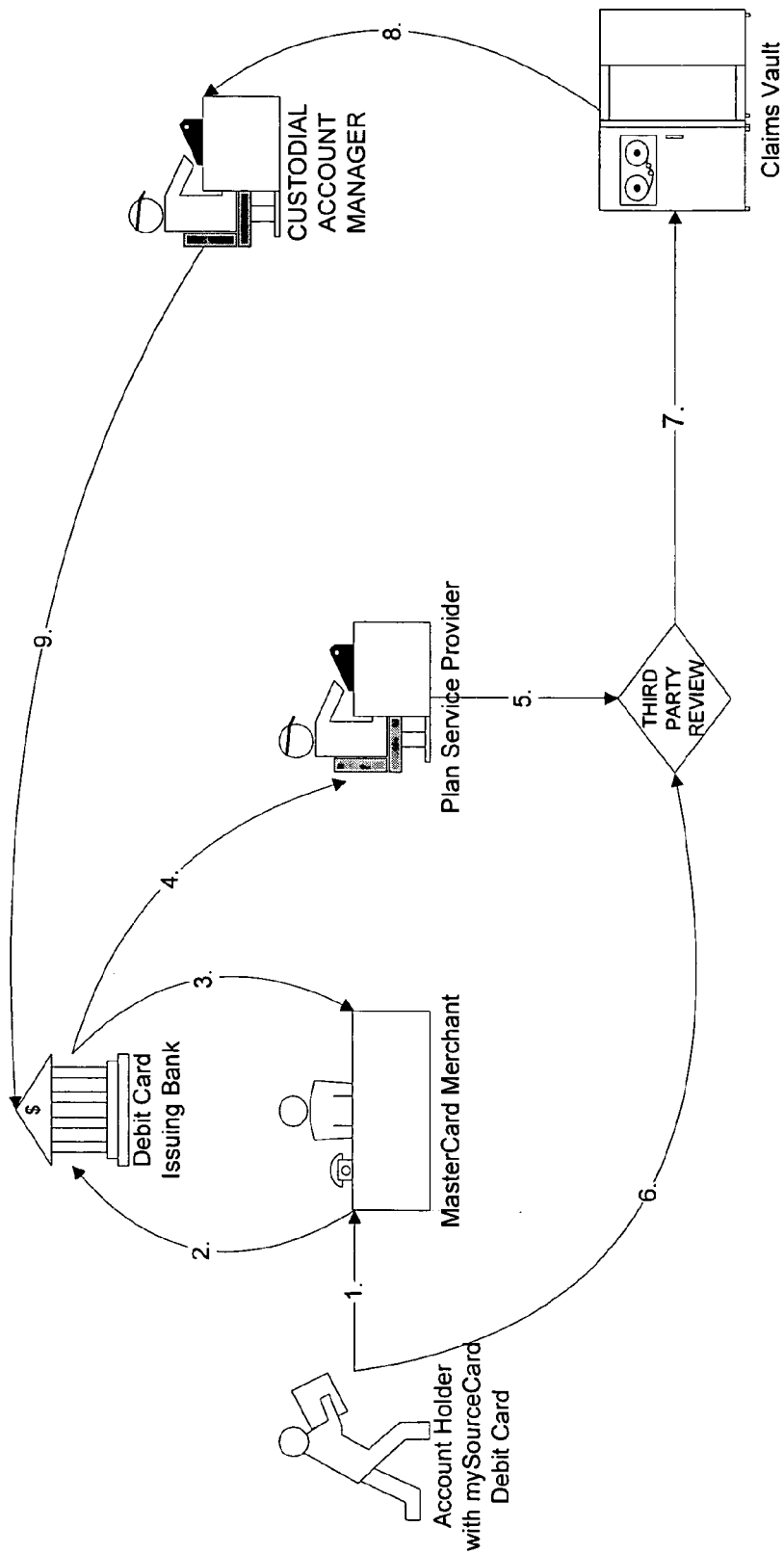

FIG. 7 is a diagram that visually illustrates various steps taken, in various embodiments of the invention, during the process of executing a debit card transaction that will be documented via a claims vault.

Figure 8:
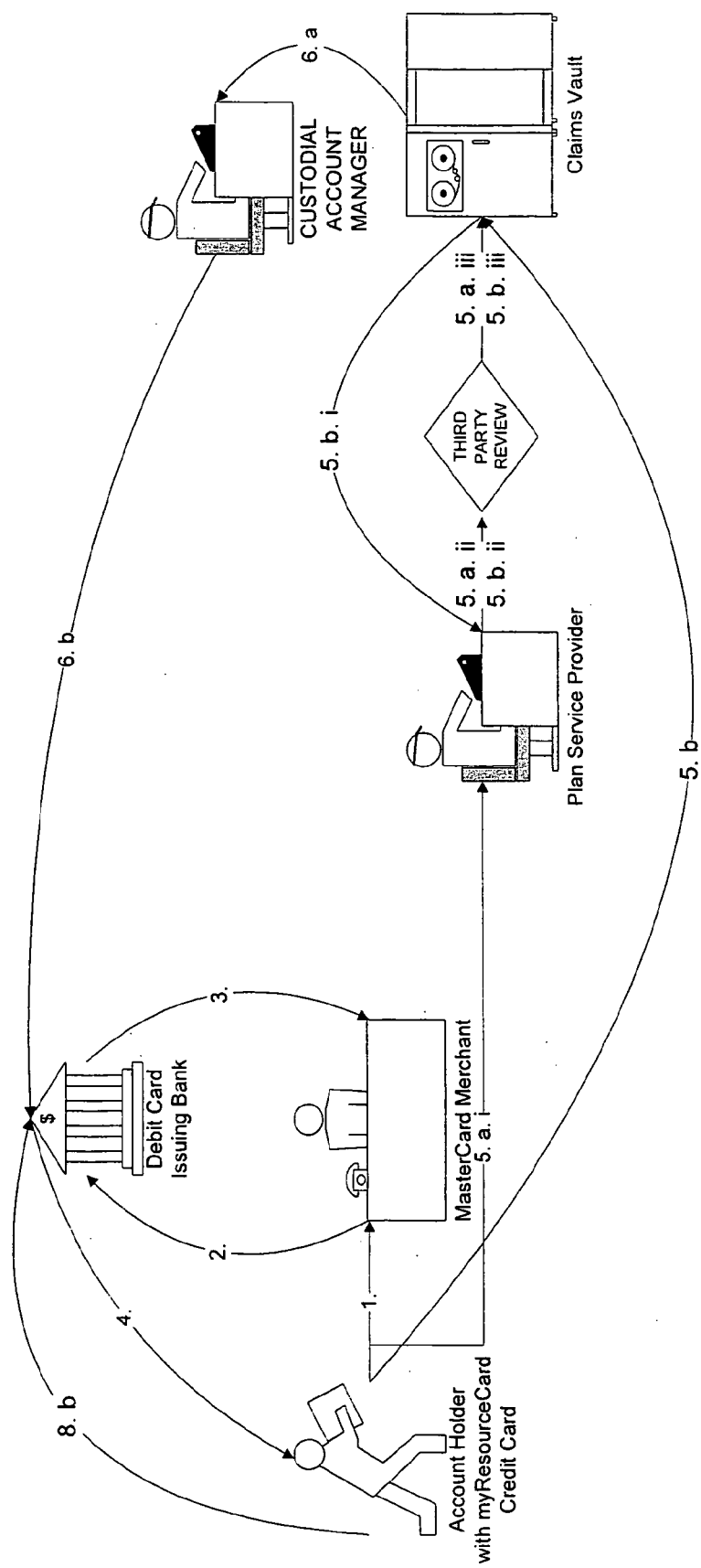

FIG. 8 is a diagram that visually illustrates various steps taken, in various embodiments of the invention, during the process of executing a credit card transaction that will be documented via a claims vault.

Figure 9:
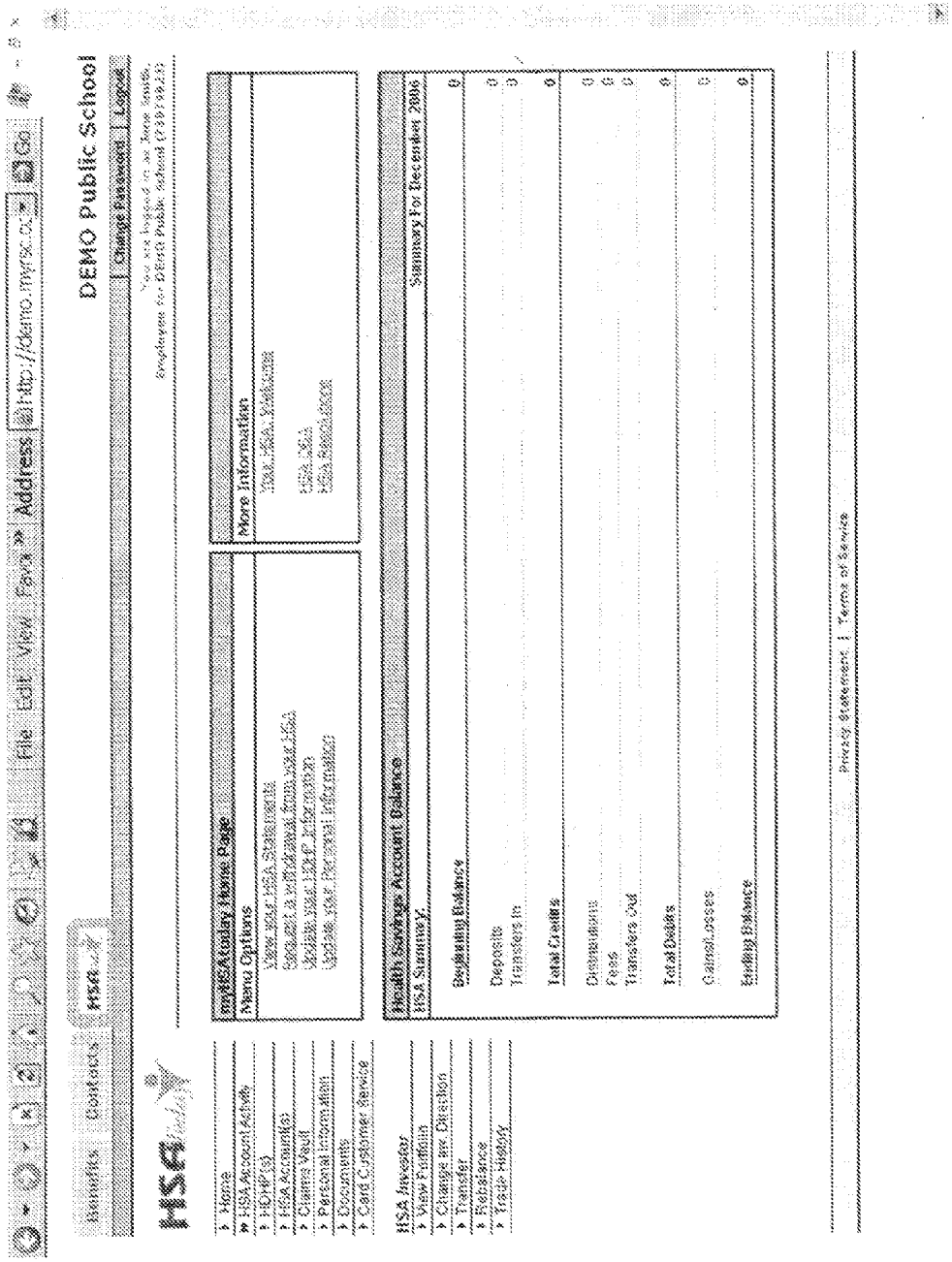

FIG. 9 depicts an account activity screen according to a particular embodiment of the invention.

Figure 10:
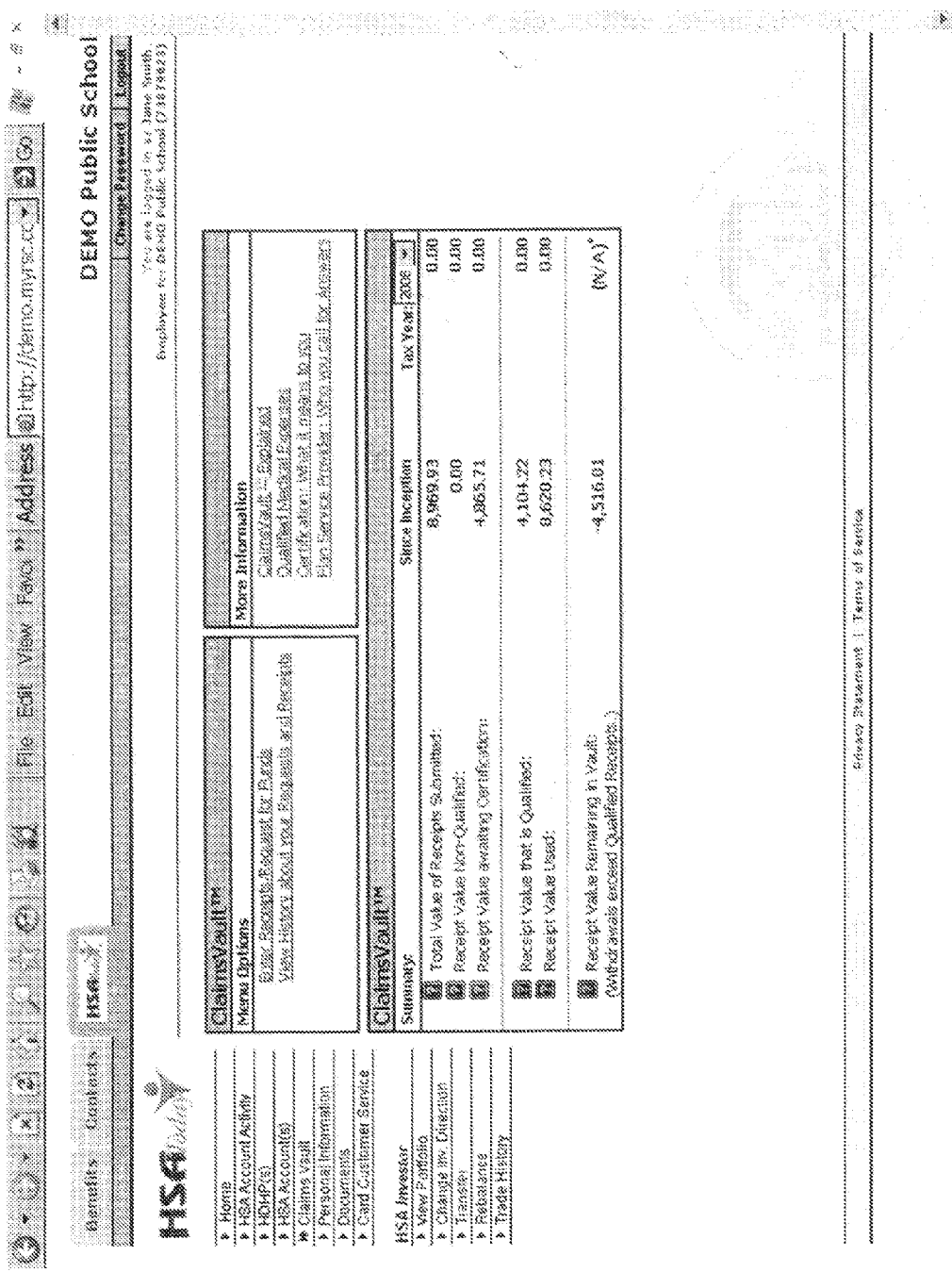

FIG. 10 depicts a claims vault summary screen according to one embodiment of the invention.

Figure 11:
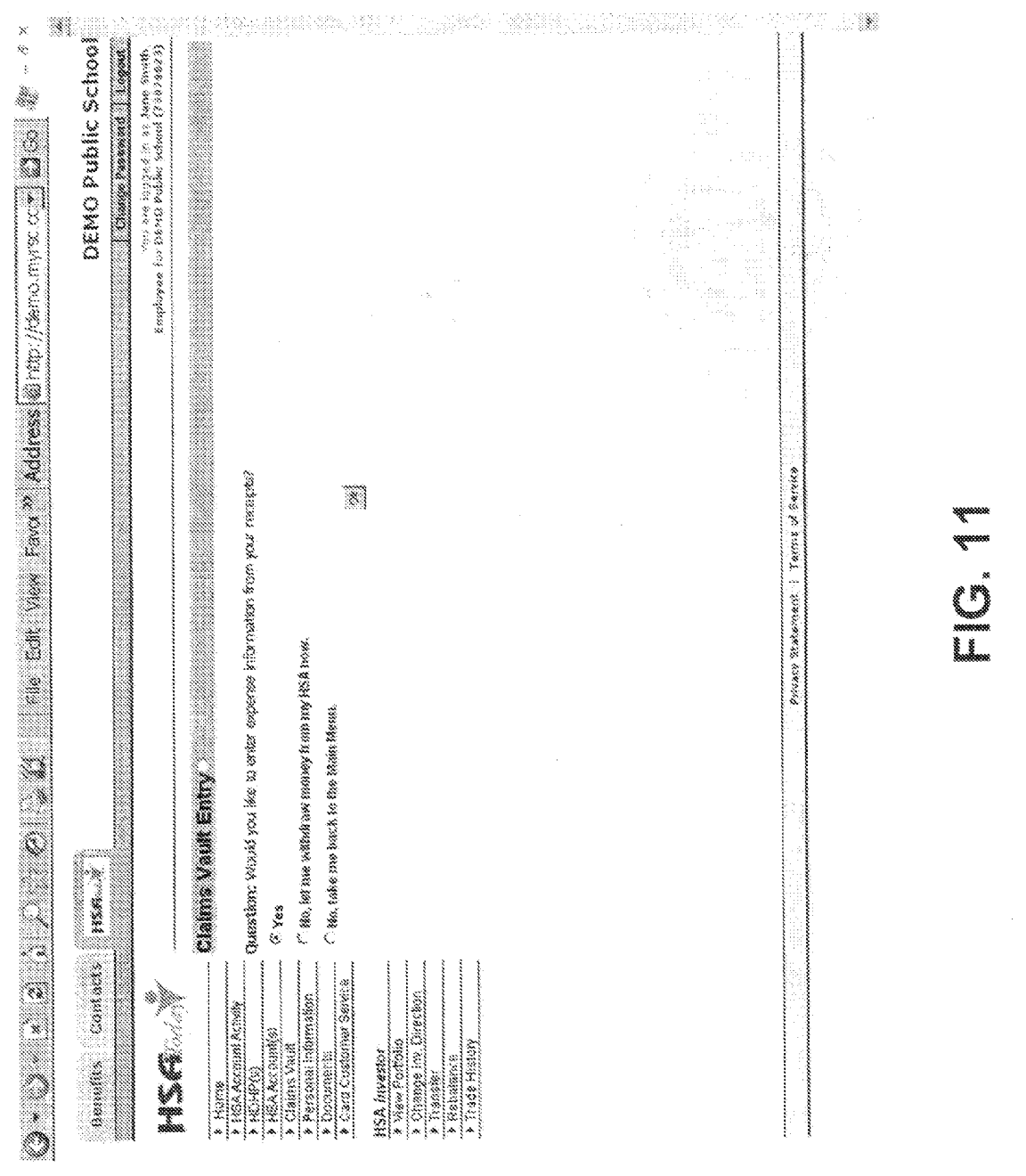

FIG. 11 depicts a claims vault entry screen according to various embodiments of the invention.

Figure 12:
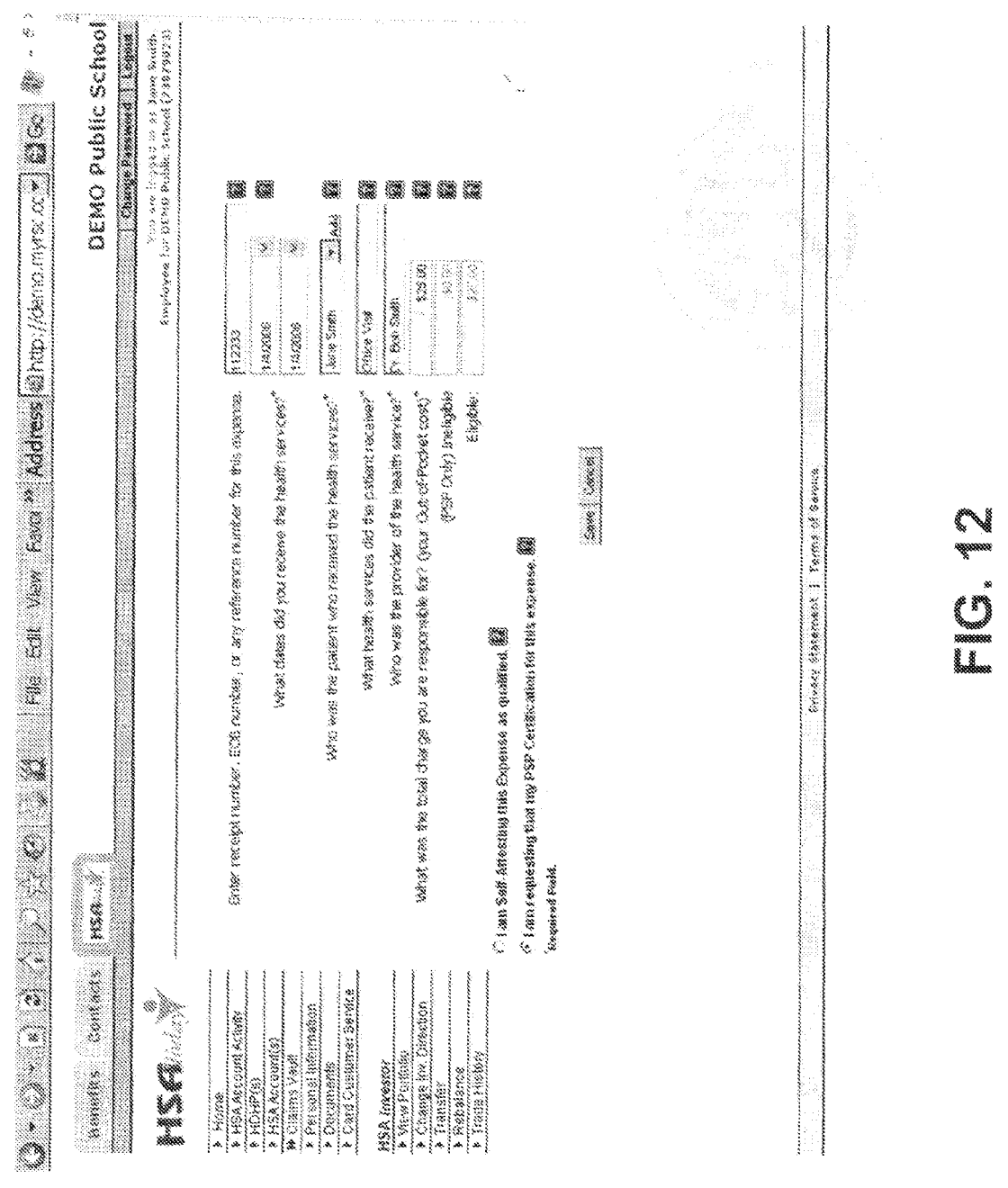

FIG. 12 depicts a claims vault receipt entry screen according to a particular embodiment of the invention.

Figure 13:
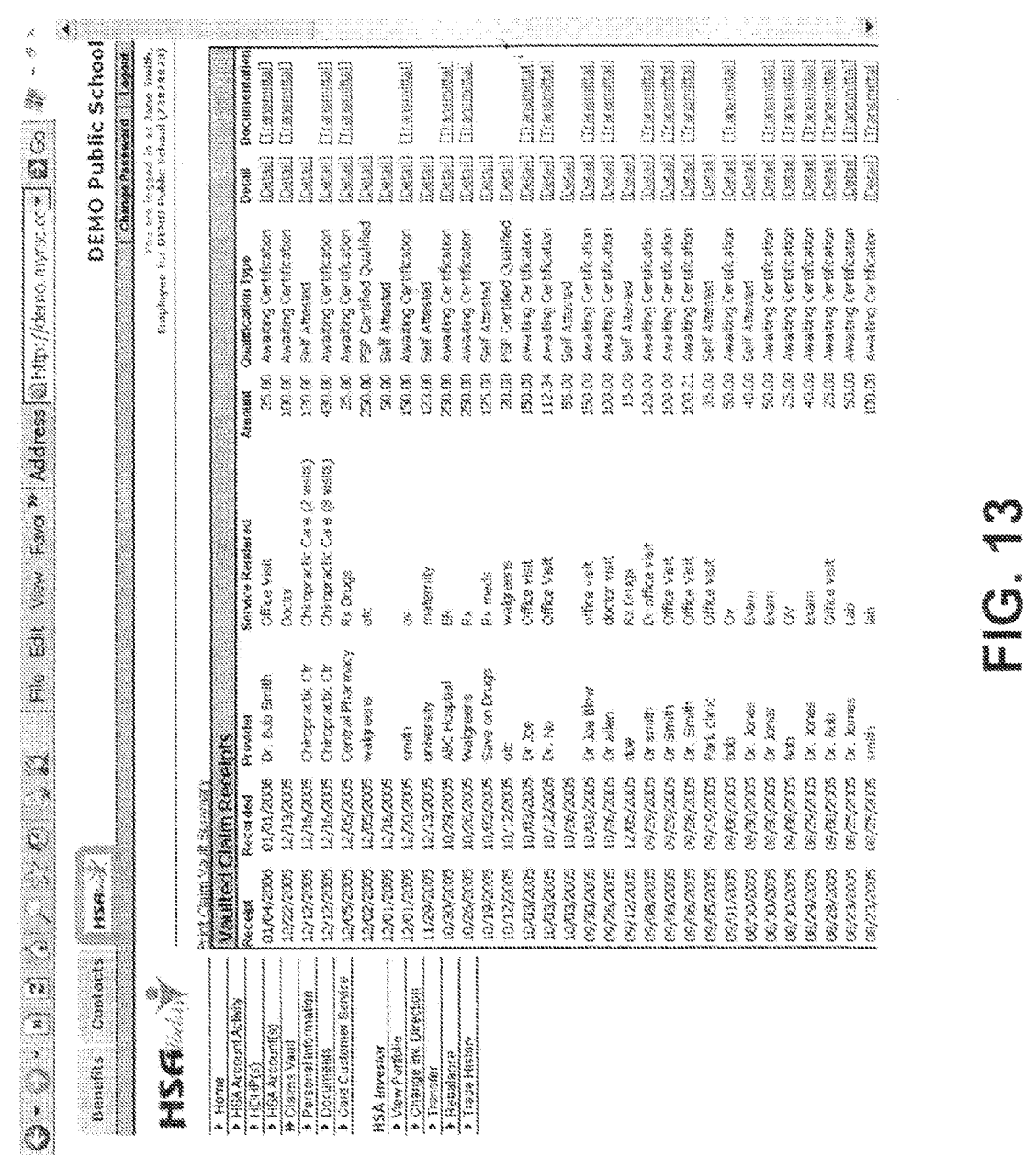

FIG. 13 depicts an upper portion of a claim vault history screen according to a particular embodiment of the invention.

Figure 14:
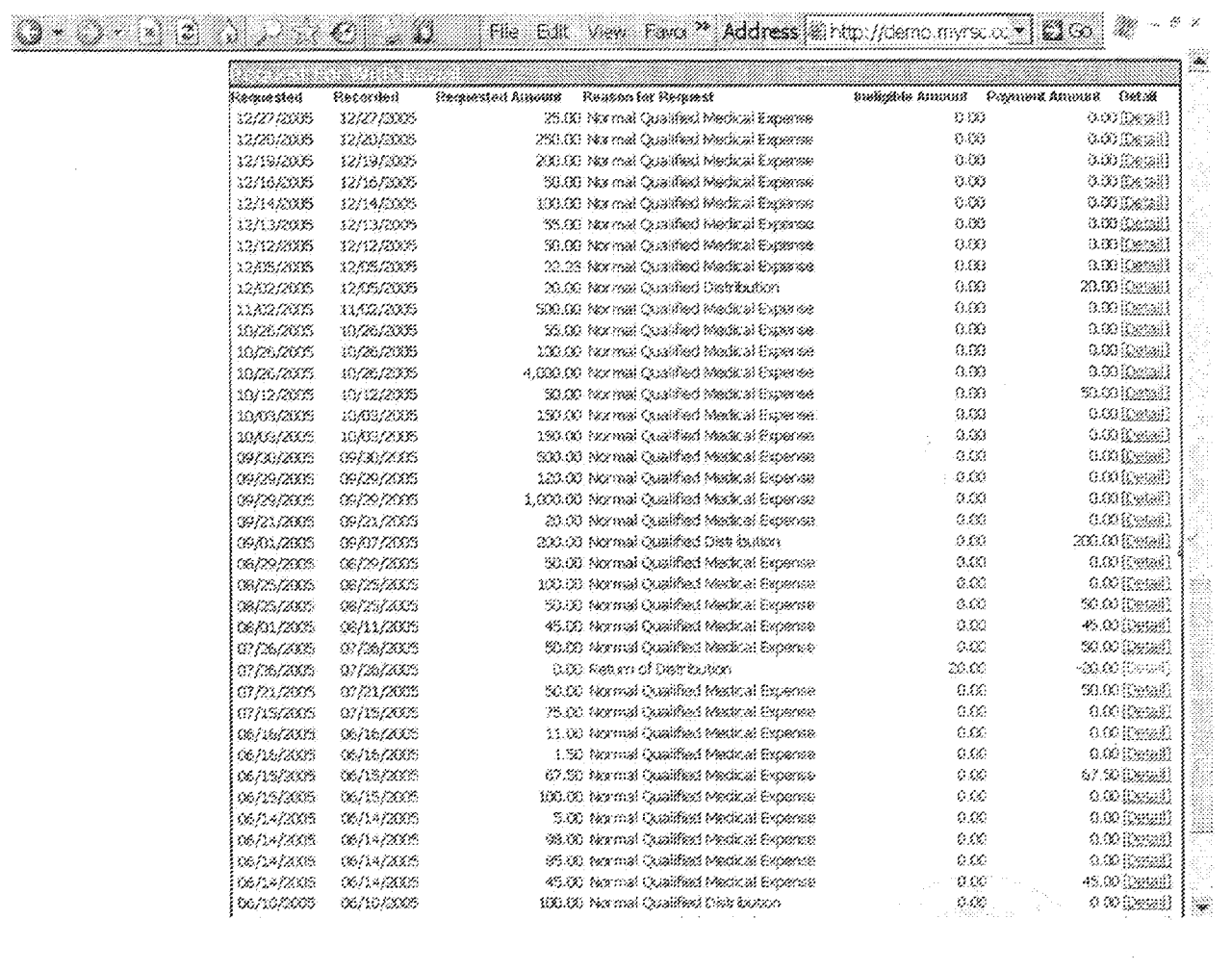

FIG. 14 depicts a lower portion of the claim vault history screen of FIG. 13.

Figure 15:
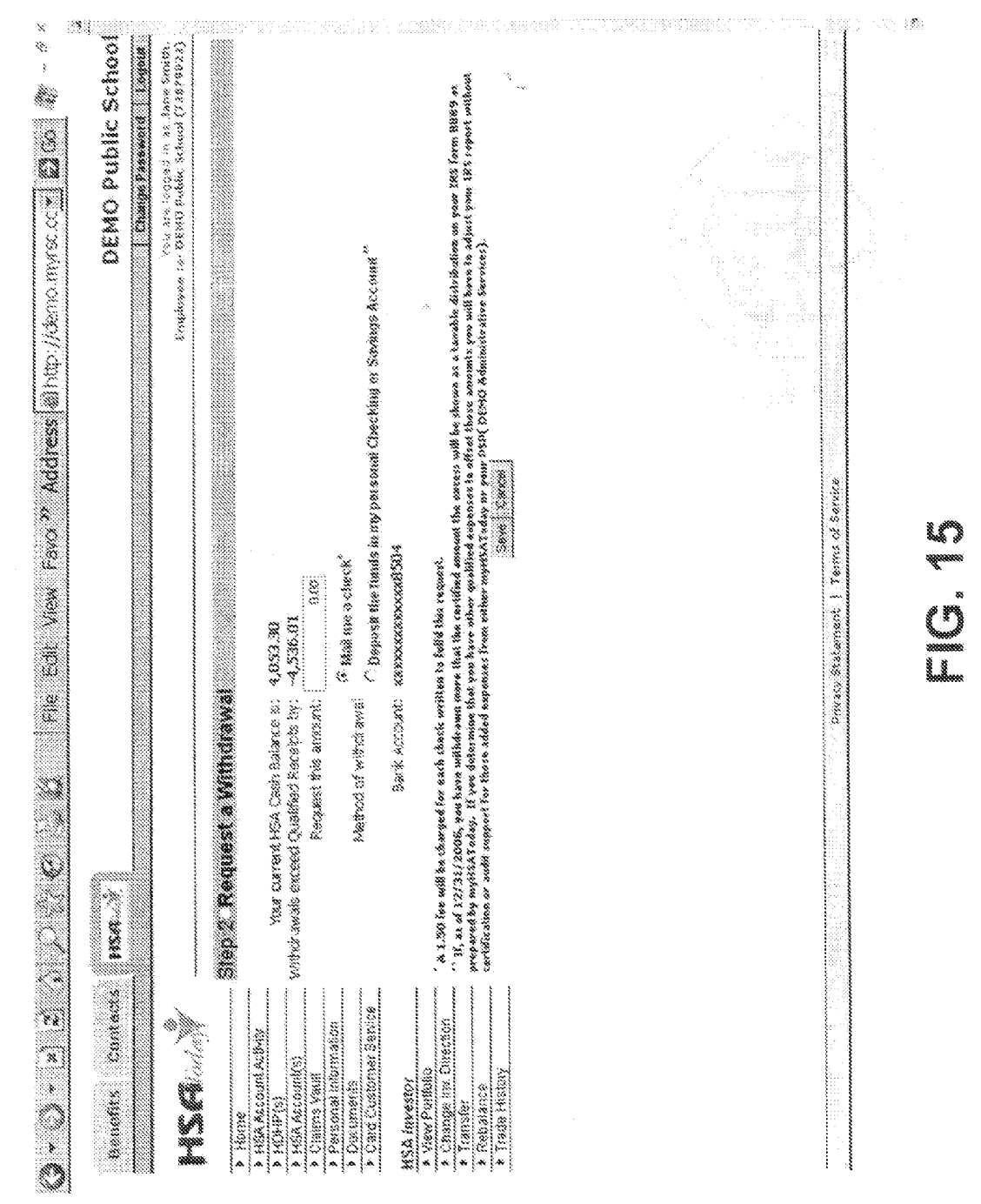

FIG. 15 depicts a withdrawal request screen according to various embodiments of the invention.

Figure 16:
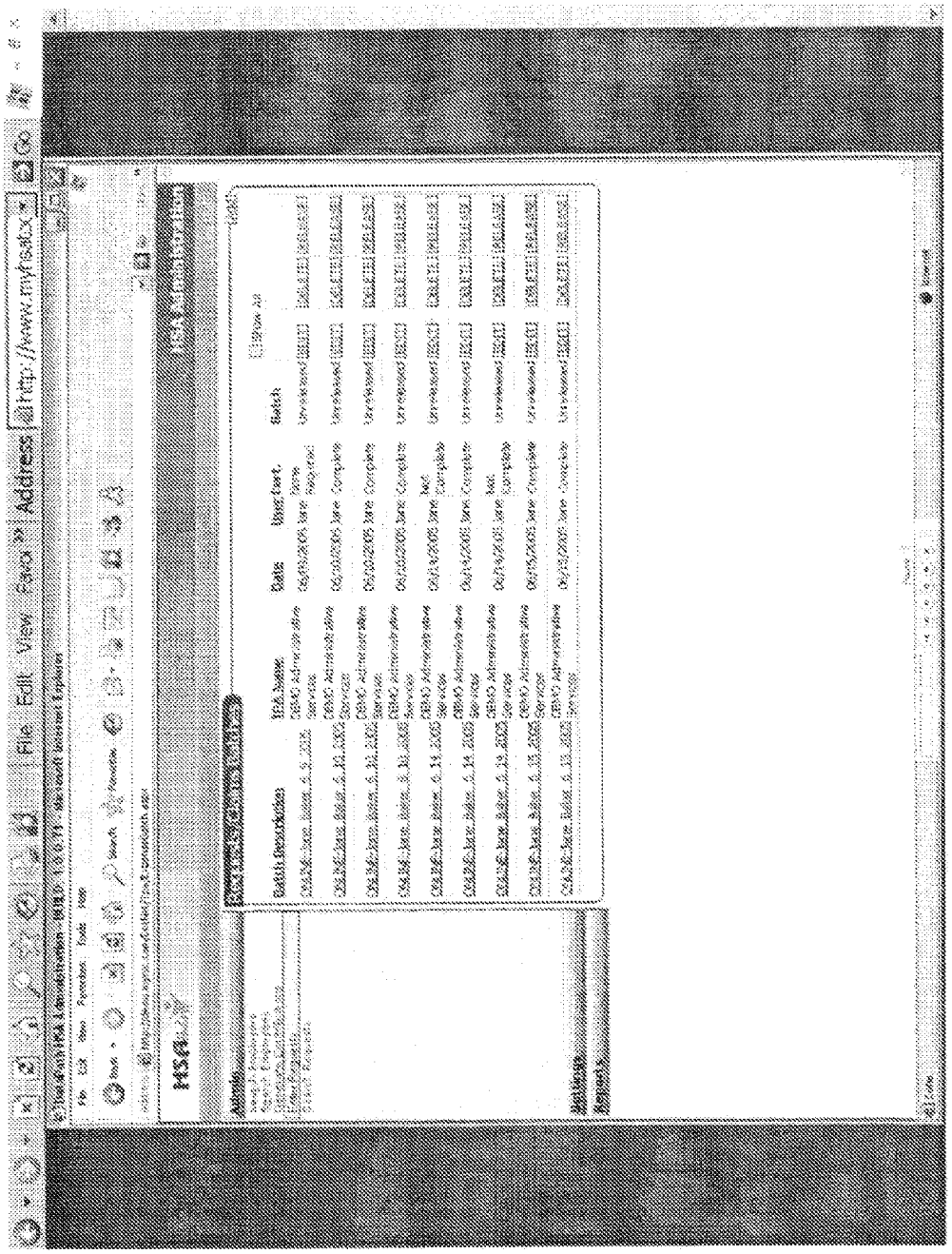

FIG. 16 depicts a first request processing screen according to a particular embodiment of the invention.

Figure 17:
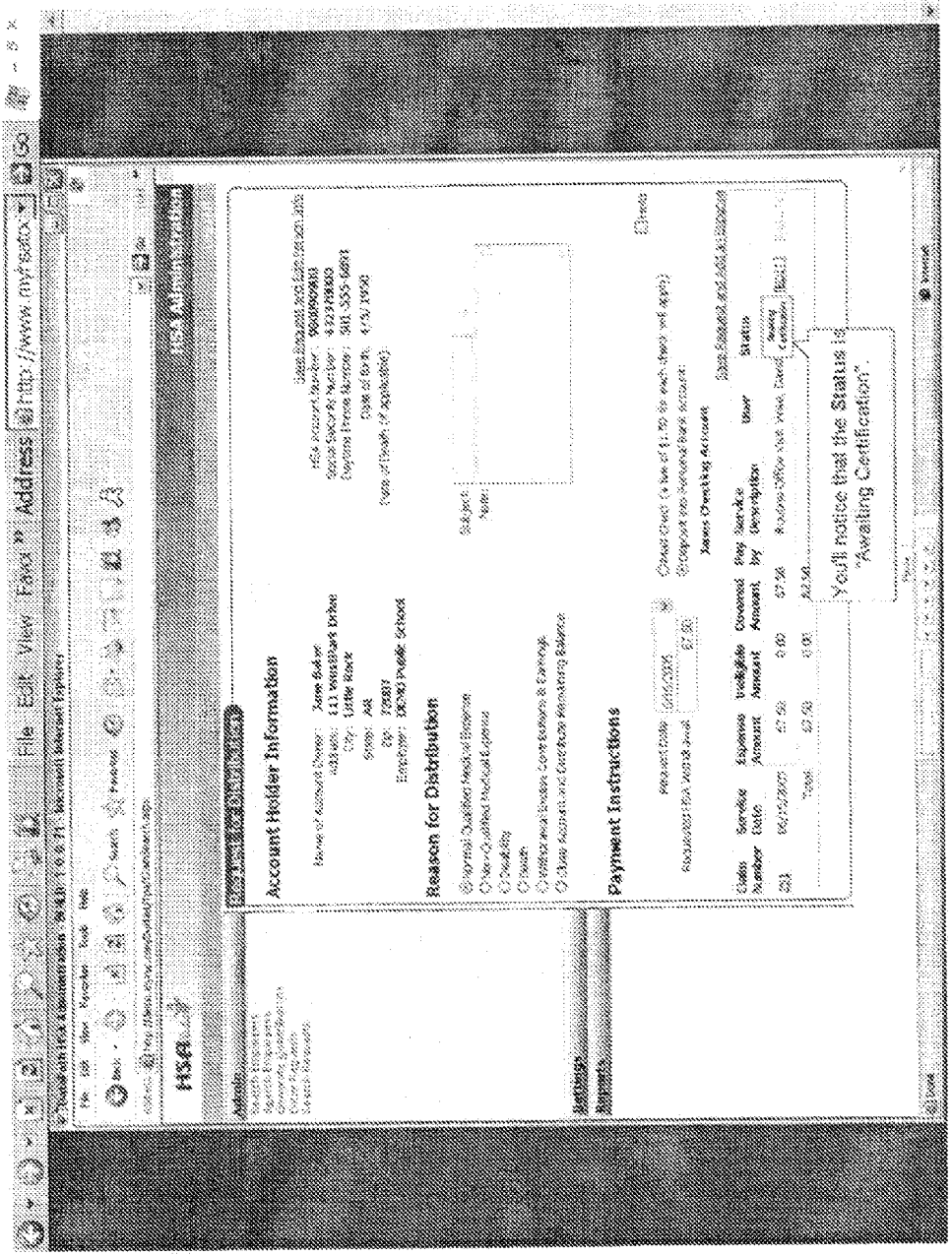

FIG. 17 depicts a second request processing screen according to various embodiments of the invention.

Figure 18:
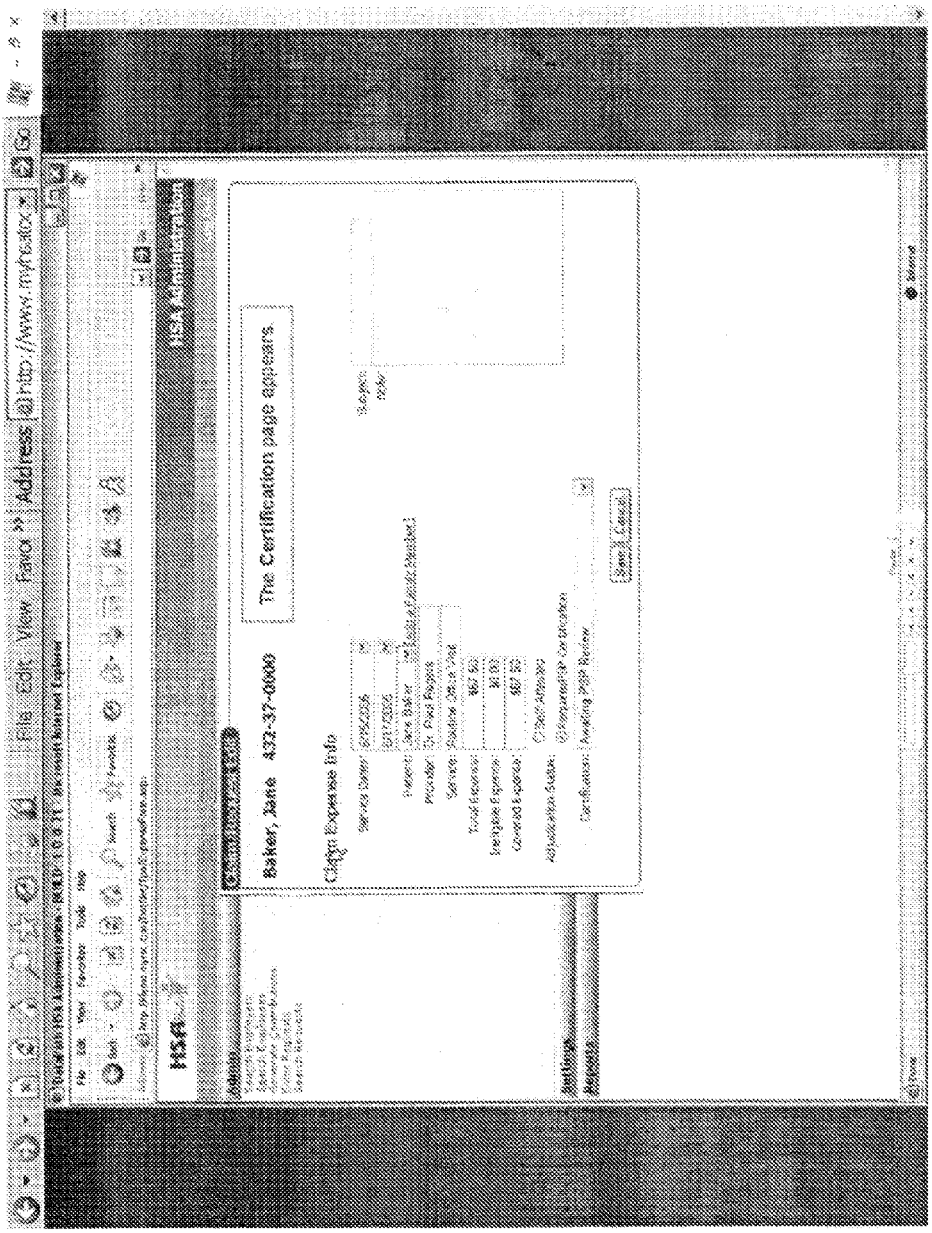

FIG. 18 depicts a request certification screen according to one embodiment of the invention.

Figure 19:
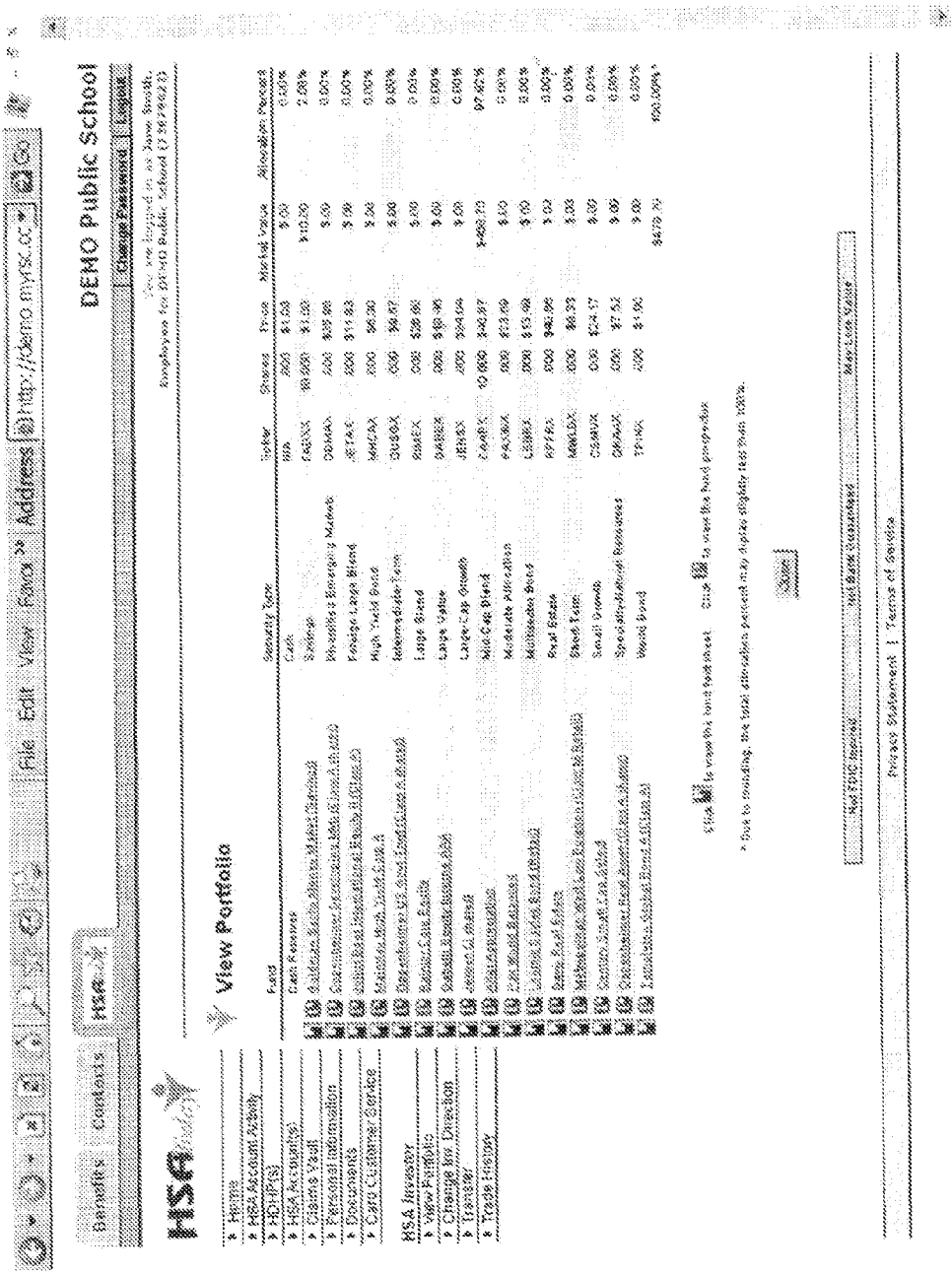

FIG. 19 depicts a portfolio summary screen according to a particular embodiment of the invention.

DETAILED DESCRIPTION OF VARIOUS EMBODIMENTS OF THE INVENTION

The present invention now will be described more fully with reference to the accompanying drawings, in which some, but not all embodiments of the invention are shown. Indeed, this invention may be embodied in many different forms and should not be construed as limited to the embodiments set forth herein. Rather, these embodiments are provided so that this disclosure will satisfy applicable legal requirements. Like numbers refer to like elements throughout.

Overview

In an account administration plan according to various embodiments of the invention, a plan service provider (PSP) acts as an intermediary between an HSA account holder and the custodian of the account holder's HSA. In certain embodiments of the invention, the PSP is trained in one or more of the following topics: insurance benefits, HSA rules and regulations, health plan administration, Personal Financial Management, ERISA, PHI, and Section 125 cafeteria plans.

In various embodiments of the invention, the PSP is contracted to function both as a customer support representative for the custodian, and as an agent for the HSA account holder (e.g., by assisting the account holder with establishing and maintaining the HSA). In certain embodiments of the invention, the PSP performs one or more of the following services: (1) providing advice to the account holder regarding the HSA (e.g., which charges are reimbursable from the HSA); (2) performing administrative services that are related to the HSA for the account holder's employer; (3) reviewing and certifying reimbursement claims (e.g., claims for reimbursement for purchases by the account holder) as being properly payable from the HSA; (4) ensuring that the account holder is covered under an HSA-qualified High Deductible Health Plan; (5) ensuring that the account holder is not covered under a non-qualifying health plan; (6) ensuring that contributions to the account holder's HSA are within allowable limits; (7) ensuring that proper documentation for distributions from the HSA are properly archived and maintained; and (8) assisting the account holder with completing tax documents involving the account holder's HSA.

In various embodiments, a PSP acts as an intermediary between various different parties, and a computer system (preferably a single computer system) is provided for facilitating the exchange of HSA account information (or other information) between such parties. For example, in various embodiments, the PSP acts as an intermediary between, and a computer system (preferably a single computer system) is provided for facilitating the exchange of HSA account information (or other information) between: (1) a custodian associated with an HSA account and an account holder associated with the HSA account ("the account holder"); (2) the account holder and the account holder's employer; (3) the account holder's employer and an insurance carrier (e.g., a health insurance carrier providing health insurance for said account holder); (4) the account holder and a pharmacy benefit manager; (5) the account holder and an independent wellness program; and/or (6) the account holder and a health support service.

In certain embodiments of the invention, a particular PSP simultaneously: (1) performs administrative services related to one or more HSA's for a particular employer; (2) provides HSA-related services to the employer's employees under the employer's HDHP; (3) provides HSA-related services to COBRA participants under the employer's HDHP; and (4) provides HSA-related services to individual HSA account holders who are not employed by the employer. In various embodiments of the invention, the PSP uses a single account administration computer system to facilitate providing these services.

In certain embodiments of the invention, the PSP may be an individual or entity that is substantially independent from the custodian. For example, the PSP may be an independent insurance agent. However, in certain embodiments, the PSP may be an employee of the custodian bank maintaining the HSA.

In various embodiments of the invention, the account administration plan is structured to allow the account holder or the PSP to change HSA custodians with minimal disruption to the administration of the account holder's HSA. In certain embodiments, because the account holder administers the HSA primarily through the PSP, changing custodians may be substantially transparent to the account holder.

Similarly, as discussed in greater detail below, in various embodiments of the invention, the account holder may elect to have funds from their HSA maintained by a plurality of different custodians. Because, in certain embodiments of the invention, the PSP may orchestrate the respective duties of the custodians, this process may also be substantially transparent to the account holder.

Account Structure

In certain embodiments of the invention, an HSA includes a transaction account and one or more investment sub-accounts. In certain embodiments of the invention, the transaction account and investment sub-accounts are structured so that any funds being deposited into, or withdrawn from, the various investment sub-accounts must pass through the transaction account. As a result, the transaction history associated with the transaction account may be used to construct a comprehensive transaction history for the HSA.

In certain embodiments of the invention, the investment sub-accounts associated with the HSA may all be maintained at the custodian bank for the HSA. Alternatively, one or more of the investment sub-accounts may be maintained at banks other than the custodian bank for the HSA. In various embodiments of the invention, the transaction account and related investment sub-accounts are structured so that any transactions between the various investment sub-accounts (e.g., intra bank transfers of funds between a first investment sub-account at a first bank and a second investment sub-account at a second bank) must pass through the transaction account.

In particular embodiments of the invention, an account administration system associated with the HSA is used to track the various transactions associated with the HSA, and for generating various reports related to the HSA. In certain embodiments of the invention, the account administration system includes an HSA account valuation tool that is adapted to assess the monetary value of each account (including investment sub-accounts) associated with the HSA at a particular point in time, and to determine a total monetary value of the HSA based the monetary value of each account associated with the HSA at that particular point in time. The account administration system may be further configured to display this total monetary value of the HSA (and/or the monetary value of each account associated with the HSA) to the user. This may be done, for example, via an appropriate web site, or via a paper report.

HSA Account Use

A brief overview of the use of an HSA according to various embodiments of the invention will now be provided. A more detailed discussion of this topic is provided in the detailed examples below.

HSA's according to the present invention may be funded in any permissible manner. For example, the account holder may arrange to have a certain amount of each of their paychecks electronically deposited directly into the HSA in a manner known in the relevant field.

In certain embodiments of the invention, once the HSA is funded, the account holder may request disbursements from the account in one or more of the following ways: (1) by completing and submitting a paper or electronic (e.g., Internet based) disbursement request form; (2) by using a debit card associated with the HSA to execute a financial transaction (e.g., to pay for a product or service that qualifies for reimbursement from the HSA); or (3) by requesting that funds be transferred from the HSA to another account (e.g., a credit card account). These various disbursement techniques will now be discussed in greater detail.

Disbursement Requests

Disbursement Requests via a Paper or Electronic Disbursement Request Form

An account holder may request that a disbursement be made from their HSA by completing and submitting a paper or electronic claim form to the PSP associated with the HSA. When completing this claim form, the account holder may indicate whether they would like the PSP to certify that a particular payment associated with the disbursement actually qualifies as a tax-free reimbursement from the HSA. If the individual indicates that they would like the PSP to certify the payment as properly reimbursable from the HSA, the PSP reviews the payment and any supporting documentation (e.g., receipts submitted by the account holder along with the disbursement request form) to determine whether the payment is properly reimbursable from the HSA. If so, the PSP certifies the payment as HSA reimbursable and arranges for the requested disbursement to be made to the account holder (e.g., via the account administration system). If the individual does not indicate that they would like the PSP to certify the payment as reimbursable from the HSA, the PSP simply arranges for the requested amount to be disbursed from the HSA as requested by the account holder.

In certain embodiments of the invention, regardless of whether the PSP certifies a payment as being properly reimbursable from the HSA, the PSP uses the account administration system to create a claim documentation record within the system's claims vault (which is discussed in greater detail below) that includes both information regarding the transaction (e.g., the transaction date and amount) and electronic copies of any available supporting documentation related to the transaction. As discussed below, the account holder may later use the claim documentation record as documentary support for the requested disbursement.

In various embodiments of the invention, the account administration system is configured to allow an account holder to request a disbursement from the HSA without providing documentation to verify that the disbursement is for a charge that is reimbursable from the account holder's HSA. In one embodiment of the invention, in this situation, the account administration system creates a corresponding claim documentation record within the system's claims vault that includes information regarding the transaction (e.g., the transaction date and amount). In certain embodiments of the invention, the account administration system is configured to then transmit a reminder to the account holder (e.g., via a paper letter or e-mail) to submit supporting documentation to the account administration system at the account holder's earliest convenience.

In various embodiments, the account holder may submit supporting documentation by manually uploading the supporting documentation to the account administration system (e.g., via the Internet), or sending paper copies to the PSP for entry into the account administration system. In various embodiments of the invention, the system is configured for storing the supporting documentation within the system's claims vault as part of the corresponding claim documentation record.

In various embodiments of the invention, the account administration system is configured to allow an account holder to request a disbursement from their HSA without assistance from the PSP associated with the account holder's HSA. For example, the account holder may simply request a disbursement from the HSA via a website associated with the account administration system.

Reimbursement Requests via Debit Card Transactions

As indicated above, a user may request reimbursement from their HSA automatically by using a debit card associated with the HSA (e.g., a mySourceCard® MasterCard® Debit Card) as part of a financial transaction (e.g., to pay for a particular product or service). In one embodiment of the invention, the account administration system is set up to categorize any charges made to the debit card as having been implicitly verified by the user as appropriate HSA charges. Accordingly, in response to the debit card being used to pay for a particular charge, funds are disbursed (e.g., substantially automatically) from the HSA and used to pay for the debit card charge. In various embodiments, information related to the transaction is then automatically stored by the account administration system (e.g., in the system's "claims vault") for later use by the account holder.

In one embodiment of the invention, in response to the account holder using a debit card associated with the HSA as part of a financial transaction, the account administration system creates a corresponding claim documentation record within the system's claims vault that includes various information regarding the transaction (e.g., the transaction amount, and the merchant I.D. and merchant category code associated with the transaction). In certain embodiments of the invention, the account administration system is configured to then transmit a reminder to the account holder (e.g., via a paper letter or e-mail) to submit supporting documentation to the account administration system at the account holder's earliest convenience. In various embodiments of the invention, the system is configured for storing any supporting documentation received from the account holder within the system's claims vault as part of the corresponding claim documentation record.

Reimbursement Requests via Credit Card Transactions

As indicated above, a user may request reimbursement from their HSA by requesting that funds be transferred from the HSA to another account (e.g., the myResourceCard® MasterCard® credit card). In one embodiment of the invention, the account administration system is configured to categorize any such disbursements as having been verified by the user as valid HSA charges. Accordingly, the requested funds are then disbursed from the HSA and transferred to the indicated account. Information related to the transaction is then stored by the account administration system (e.g., in the system's "claims vault") for later use by the account holder.

In one embodiment of the invention, in response to the account holder requesting that funds be transferred from the HSA to a particular account (e.g., a credit card account), the account administration system creates a corresponding claim documentation record within the claims vault that includes various information regarding the transaction (e.g., the transaction amount, and the merchant I.D. and merchant category code associated with the transaction). In certain embodiments of the invention, the account administration system is configured to then transmit a reminder to the account holder (e.g., via a paper letter or e-mail) to submit supporting documentation to the account administration system at the account holder's earliest convenience. In various embodiments of the invention, the system is configured for storing any supporting documentation received from the account holder within the system's claims vault as part of the corresponding claim documentation record.

Claims Vault

As noted above, the account administration system may include a "claims vault" module ("claims vault") that is adapted to receive documentation to support a future reimbursement claim from an account holder's HSA, and to store this information for later use by the account holder. This supporting documentation may include, for example, receipts verifying that a payment is qualified for reimbursement from the HSA. Entries into the claims vault, in addition to direct data entry by the account holder or the PSP, may come by way of an electronic Explanation of Benefits ("EOB") from a health insurance carrier, a health claims third party administrator ("Health TPA"), a pharmacy benefit manager ("PBM") or from another source.

To use the claims vault feature of an account administration system according to one embodiment of the invention, the account holder may submit, to the PSP, paper copies of supporting documentation for reimbursement of a particular payment made by the account holder. The account holder may also include a reimbursement claim form specifying that the account holder would like to store the supporting documentation in the account administration system's claims vault. For example, the account holder may submit a receipt for medical supplies to the PSP along with a form indicating that the account holder wishes to store the supporting documentation in the account administration system's claims vault.

In response to receiving these documents from the account holder, the PSP verifies that the payment at issue is a payment that qualifies for reimbursement from the HSA. The PSP then converts the submitted supporting documentation into electronic format (e.g., via an electronic document scanner) and stores the electronic version of the supporting documentation in the system's claims vault (which, in one embodiment of the invention, includes a database). In certain embodiments of the invention, the system also stores, within the claim vault, an electronic summary of the claim. This electronic claim summary may be electronically associated with the corresponding electronic copy of the related supporting documentation and then stored, along with the corresponding electronic copy of the supporting documentation, as a claims documentation record within the system's claims vault.

As noted above, in various embodiments of the invention, the claims vault may be adapted to store electronic versions of supporting documentation and related claim information for later submission by the account holder in support of a disbursement request from the HSA. This may allow the user to store supporting documentation within the claims vault for various claims as the account holder makes HSA qualified payments. The account holder may then wait to file a request for reimbursement for the payments until which later time the account holder wishes to physically receive the actual reimbursement for the payments. In a particular embodiment of the invention, this allows the account holder to keep funds in their HSA (and to accumulate tax-deferred interest on the funds), even after the account holder has made a payment that will eventually be reimbursed by the funds. In various embodiments of the invention, the system is configured to facilitate submission of supporting documentation for a particular payment a plurality of months (and preferably a plurality of years) after the payment was made. The submission may be made along with a claim requesting reimbursement for the charge from the account holder's HSA.

Association of Disbursements with Claims

In various embodiments of the invention, the account administration system is configured to allow account holders to manually associate disbursements made from the HSA with claim documentation records that are stored in the claims vault. The account holder may do this, for example, via a web site associated with the account administration system. More specifically, the account holder may use the web site's graphical user interface to manually associate a particular HSA disbursement with one or more claim documentation records stored in the claims vault. Documentation from the claims vault may later be used to support a corresponding HSA disbursement.

In various embodiments of the invention, the system is configured to automatically reconcile any disbursements made from an account holder's HSA that are not associated with supporting documentation, with claim documentation records (including associated supporting documentation) that are stored within the claims vault associated with the HSA. For example, in certain embodiments of the invention, the system is configured to automatically associate, on a first-in-first-out basis, any disbursements made from the HSA that are not associated with supporting documentation, with claim documentation records (and associated supporting documentation) that are stored within the claims vault associated with the HSA. This may be done, for example, at the end of each calendar year. For example, if: (1) the oldest unsupported disbursement for a particular HSA during a particular year were a disbursement of $70.00; and (2) the oldest claim documentation record within the HSA's claims bank that was not already associated with a disbursement were related to a non-reimbursed payment of $70.00, the system would associate the $70.00 disbursement with the $70.00 claim documentation record.

In a particular embodiment of the invention, the account holder or the PSP can run a disbursement association program to arrange (e.g., by date of service) any claim documentation records for the current plan year that are stored within the HSA's claims vault and that are not associated with a corresponding disbursement. The system then associates these claim documentation records with disbursements from the HSA on a first-in-first-out basis. This association serves as a "tie" between the disbursement and the supporting claim documentation record used to substantiate the fact that the disbursement was a qualified HSA disbursement.

In one embodiment of the invention, if, after the above disbursement association program has run, the account holder enters a new claim record into the claims vault for a qualified expense not previously documented by a claim documentation record in the claims vault, the disbursement association program can be run again as discussed above. In various embodiments, the disbursement association program is available until the close out date for HSA filing with the IRS by the Custodian. At that time, the various associations between disbursements and claim documentation records will be saved and associated with the custodian's current HSA filing with the IRS. In various embodiments of the invention, it is possible to modify the associations between disbursements and claim documentation records after a particular HSA filing is made for a particular year. However, this typically requires the custodian to make an amended filing with the IRS.

In certain embodiments of the invention, the disbursement association program is provided as an optional service to the HSA account holder. In various embodiments of the invention, the account administration system is adapted to generate reports based on the disbursement association program that include sufficient detail to allow the PSP to guarantee IRS compliance to the account holder.

Additional Parties

Although the various parties that are described above as being associated with the administration of a particular HSA are limited to the account holder, a plan service provider (PSP), and the custodian of the HSA, other parties may also be associated with the administration of a particular HSA. For example, the custodian of a particular HSA may hire a custodian account manager to manage various aspects of the HSA. Alternatively, the custodian may manage the HSA in-house.

Similarly, a registered investment advisor may be used to help determine how funds within the HSA are to be invested. For example, in one embodiment of the invention, the custodian of the HSA may make a registered investment advisor available to the account holder: (1) to provide advice to the account holder regarding how funds from the HSA should be invested; and/or (2) to invest funds from the HSA on behalf of the account holder. Accordingly, in various embodiments of the invention, the funds within the HSA may be invested: (1) by the account holder without assistance from a registered investment advisor; (2) by the account holder with guidance from a registered investment advisor; or (3) by a registered investment advisor substantially without input from the account holder.

In certain embodiments of the invention, the custodian may require an account holder to consult with a registered investment advisor before investing funds from the HSA in certain types of investments, such as individual stocks or bonds.

Based on the above, it should be understood that one unique aspect of systems and plans according to various embodiments of the invention is that they simultaneously support multiple custodians, multiple PSPs, multiple employers, associations of employers, and/or groups of non-related, non-employee individuals. In various embodiments of the invention, one or more of the individual account holders has a single HSA transaction account with multiple HSA investment sub-accounts from multiple investment firms and/or funds.

Structure of an Exemplary Account Administration System

A system 5 according to one embodiment of the invention is shown in FIG. 1. As may be understood from this figure, in this embodiment, the system 5 includes at least one account holder computer 10 that is connected (e.g., via a network 15 such as a LAN or a global communications network, such as the Internet) to communicate with an account administration server 20. The system may also include other computers that are connected (e.g., via a network 15 such as a LAN or a global communications network, such as the Internet) to communicate with the account administration server 20. Such computers may include, for example: (1) one or more PSP computers 25 (e.g., computers that are associated with one or more plan service providers); (2) one or more custodian account manager computers 30 (e.g., computers that are associated with one or more custodian account managers); (3) one or more custodian computers 35 (e.g., computers that are associated with one or more account custodians); (4) one or more registered investment advisor computers 40 (e.g., computers that are associated with one or more registered investment advisors); (5) one or more insurance carrier computers (e.g., computers that are associated with one or more insurance carriers); (6) one or more health TPA computers (e.g., computers that are associated with one or more health TPA's); and (7) one or more PBM computers (e.g., computers that are associated with one or more PBM's). The system may be further connected to communicate with one or more merchant terminals 45.

In various embodiments of the invention, the account administration system is configured to allow one or more of the following parties to access (preferably simultaneously) information from a particular HSA account: (1) the HSA account holder; (2) one or more custodians of the HSA; (3) a PSP associated with the HSA; (4) one or more registered investment advisors associated with the HSA; and (5) one or more custodian account managers. In various embodiments of the invention, the account administration system is configured to allow one or more of the above parties to manage the HSA via the account administration system. In addition, the certain embodiments of the invention, the system is configured to provide the above access and management functionality for multiple HSA accounts. In certain embodiments of the invention, a first plurality of these multiple HSA accounts may be associated with a first employer, and a second plurality of these multiple HSA account may be associated with a second employer.

In one embodiment of the invention, the account administration server 20 is configured for retrieving data from, and for saving data to, a database 22 that may be stored on (or, alternatively, stored remotely from) the account administration server 20. In the embodiment shown in FIG. 1, the database 22 is maintained on a computer that is remote from the account administration server 20.

FIG. 2 shows a schematic diagram of an account administration server 20 according to one embodiment of the invention. As may be understood from this figure, in this embodiment, the account administration server 20 includes a processor 60 that communicates with other elements within the account administration server 20 via a system interface or bus 61. Also included in the account administration server 20 is a display device/input device 64 for receiving and displaying data. This display device/input device 64 may be, for example, a keyboard or pointing device that is used in combination with a monitor. The account administration server 20 further includes memory 66, which preferably includes both read only memory (ROM) 65 and random access memory (RAM) 67. The server's ROM 65 is used to store a basic input/output system 26 (BIOS), containing the basic routines that help to transfer information between elements within the account administration server 20.

In addition, the account administration server 20 includes at least one storage device 63, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 63 is connected to the system bus 61 by an appropriate interface. The storage devices 63 and their associated computer-readable media provide nonvolatile storage for a personal computer. It is important to note that the computer-readable media described above could be replaced by any other type of computer-readable media known in the art. Such media include, for example, magnetic cassettes, flash memory cards, digital video disks, and Bernoulli cartridges.

A number of program modules may be stored by the various storage devices and within RAM 67. Such program modules include an operating system 80, a substantiation module 200 and a reimbursement module 300. The substantiation module 200 and the reimbursement module 300 control certain aspects of the operation of the account administration server 20, with the assistance of the processor 60 and an operating system 80.

Also located within the account administration server 20 is a network interface 74, for interfacing and communicating with other elements of a computer network. It will be appreciated by one of ordinary skill in the art that one or more of the account administration server 20 components may be located geographically remotely from other account administration server 20 components. Furthermore, one or more of the components may be combined, and additional components performing functions described herein may be included in the account administration server 20.

HSA Account Portability

As noted above, in various embodiments of the invention, the account administration system is configured to store records for the HSA account holder over the course of many years, regardless of the account holder's employment status. Accordingly, in various embodiments of the invention, the HSA is portable between employers and may be maintained by the account holder even if the account holder becomes unemployed. In certain embodiments of the invention, the HSA is configured to be maintained by an account holder without regard to: (1) their employer; (2) their employer's HSA custodian; and/or (3) their account holder's health care insurance policy.

EXEMPLARY SYSTEMS AND METHODS

Below is a description of various systems and methods according to particular embodiments of the invention. In particular, the description provides a detailed discussion of how an HSA is set up and maintained in a particular embodiment of the invention.

Establishing an HSA Account

FIG. 3 demonstrates a process for establishing an HSA according to one embodiment of the invention. This process includes the following steps, which are cross-referenced by number in FIG. 3.

1. The PSP provides an employer with an Employer Information & Funding Form. This form provides the PSP with general information about the employer, pre-tax or post-tax designation for contributions of the prospective account holders, and permissible techniques for funding the account (e.g., by check, electronic funds transfer ("EFT"), or wire transfer).
2. The PSP provides prospective Account Holders with an HSAToday™ Enrollment Packet containing the following:
   a. A Custodial Account Agreement that includes the terms and conditions of the HSA as well as the responsibilities of the various parties to that agreement. This agreement includes a description of the role that the PSP will have in managing the HSA.
   b. An Application & Beneficiary Designation Form ("Application") that provides basic information about the account holder. This form identifies the PSP by name and provides the PSP's address and contact information.
   c. A fee schedule that details the various fees associated with the HSA.
   d. A Salary Reduction Agreement that can be customized by the PSP and that allows the account holder to make contributions to their HSA by means of a pre-tax payment through their employer's cafeteria plan.
   e. A Scheduled Contribution Worksheet that allows individuals who are not participating in their employer's cafeteria plan to make contributions to their HSA from either their personal checking/savings account or through payroll.
   f. Other forms as determined by the PSP.
3. The PSP receives the completed Application and Salary Reduction Agreement or Scheduled Contribution Worksheet from a prospective account holder and enters the information from these documents into the account administration system.
4. The PSP then forwards the application to a custodial account manager for final review.
5. The custodial account manager establishes the account with the custodian.

Making Contributions to the HSA

FIG. 4 demonstrates a process for making contributions to an HSA according to one embodiment of the invention. This process includes the following steps, which are cross-referenced by number in FIG. 4.

1. The PSP receives a payroll contribution report along with funds from the account holder's employer for deposit into the HSA.
2. The PSP uses the account administration system's administration functionality to record and reconcile monthly contributions into the HSA (e.g., contributions made via a payroll contribution from the account holder or via a contribution from the account holder's employer).
3. The PSP uses the account administration system to electronically transfer information regarding the contributions for the account holder to the custodial account manager. This information includes the amount and source of the account holder's contributions.
4. The custodial account manager electronically debits the account designated by the PSP for contributions made to the HSA.
5. The custodial account manager electronically transfers the contributions to the custodian and credits the HSA by the amount of the contribution.

Making Distributions from the HSA

FIG. 5 demonstrates a process for making distributions from an HSA according to one embodiment of the invention. This process includes the following steps, which are cross-referenced by number in FIG. 5.

1. The PSP receives a distribution request form from the account holder that lists a requested distribution and that indicates whether the distribution is for a qualified expense.
2. The PSP reviews the request and accompanying supporting documentation (if any). If the expense is a qualified expense, the PSP certifies the expense to be a qualified expense.
3. The PSP enters the request in the administration system along with the supporting documentation (if any).
4. The PSP instructs the custodial account manager to make the requested distribution (e.g., via an electronic funds transfer or check).
5. The custodial account manager withdraws the requested amount from the account holder's HSA with the custodian.
6. The withdrawn funds are then sent to the account holder via EFT or by check as instructed by the PSP.

Storing a Claim Documentation Record in the Claims Vault when the Charge Underlying the Related Claim is Not Made via a Debit or Credit Card FIG. 6 demonstrates two processes for storing a claim documentation record in the claims vault when the charge underlying the claim documentation record is not made via a debit or credit card. The first process involves entry of the claim by the PSP. The second process involves entry of the claim by the account holder, followed by third-party review by the PSP. The various steps listed below are cross-referenced by number in FIG. 6.

Process 1: Entry of Claim Documentation Record by PSP

1. The account holder incurs a qualified medical expense and submits a receipt and/or other supporting documentation to the PSP (e.g., via fax, mail, or e-mail).

2. The PSP reviews the receipt and/or supporting documentation to determine whether the expense is a qualified expense under Section 213(d).
3. If the PSP determines that the expense is a qualified expense under 213(d), the PSP enters the medical expense information into the account administration system, which stores the information (including an electronic copy of the submitted receipts and other supporting documentation) in the claims vault for later use.

Process 2: Entry of Claim by Account Holder Followed by Third Party Review by the PSP 1. The account holder incurs a qualified medical expense and electronically enters the related medical information and supporting documentation into the account administration system (e.g., via an electronic document scanner). The account administration system stores this information in the system's claims vault. If the claim is "self attested" by the account holder as a qualified medical expense, the process ends here.
2. If the account holder requests review by the PSP for "third party certification", notification is passed (e.g., via the account administration system) to the PSP to review the posted information.
3. The PSP uses the account administration system to review the posted information. If necessary, the PSP requests, via the account administration system, that the employee submit additional documentation to either the PSP for processing or directly to the system's claims vault for PSP review.
4. The PSP reviews the receipt and/or other supporting documentation to determine whether the expense is a qualified expense under Section 213(d).
5. If the PSP determines that the expense is a qualified expense under 213(d), the PSP enters the medical expense information into the account administration system, which stores the information (including an electronic copy of the submitted receipts and other supporting documentation) in the system's claims vault for later use.

Processing a Debit Card Transaction

FIG. 7 demonstrates a process, according to a particular embodiment of the invention, for using the account administration system to process a debit card transaction. This process includes the following steps, which are cross-referenced by number in FIG. 7.

1. The account holder uses a debit card associated with the account administration system at an approved merchant.
2. The merchant uses a Point of Sale (POS) machine to request authorization for the transaction from the debt card's issuing bank.
3. The transaction is approved and the merchant is paid pursuant to standard debit card payment card procedures.
4. Information regarding the approved debit card transaction is sent to the PSP via electronic download through a debit card service, such as myRSC.com debit card services.
5. The PSP processes the transaction and performs a third party review for eligibility as a Section 213(d) expense.
6. The account holder may send documentation to further support the transaction to the PSP for further review.
7. If the PSP determines that the expense is a qualified expense under 213(d), the PSP enters the medical expense information into the account administration system, which stores the information (including an electronic copy of the submitted receipts and other supporting documentation) in the system's claims vault for later use.
8. The account administration system releases the requested funds from the custodian to the custodial account manager for processing.
9. Since the distribution is based on a debit card swipe, the funds are sent to the issuing bank associated with the debit card.

Processing a Credit Card Transaction

FIG. 8 demonstrates a process, according to a particular embodiment of the invention, for using the account administration system to process a credit card transaction. This process includes the following steps, which are cross-referenced by number in FIG. 8.

1. The account holder uses a credit card (e.g., the myResourceCard MasterCard® Credit Card) at a merchant.
2. The merchant uses a Point of Sale (POS) machine to request authorization for the transaction from the credit card's issuing bank.
3. The transaction is approved and the merchant is paid pursuant to standard credit card payment card procedures.
4. The account holder receives a monthly statement from the issuing bank for all card transactions.
5. To enter a claim documentation record into the account administration system's claims vault:
   a. If the account holder wants the PSP to enter the claim:
      i. The account holder sends a claim form to the PSP for review along with related supporting documentation. The claim form indicates whether the account holder would like the distribution to be automatic or deferred.
      ii. The PSP reviews the materials received from the account holder, processes the transaction, and performs a third party review for eligibility as a Section 213(d) expense.
      iii. If the PSP determines that the expense is a qualified expense under 213(d), the PSP enters the medical expense information into the account administration system, which stores the information (including an electronic copy of the submitted receipts and other supporting documentation) in the claims vault for later use.
   b. If the account holder wants to enter the claim, the Account Holder simply uses the account administration system to manually enter the claim into the claims vault. However, if the account holder specifies that they would like the PSP to certify the transaction as properly reimbursable from the HSA:
      i. The account administration system notifies the PSP that the account holder has manually entered a claim and is requesting PSP Certification;
      ii. The PSP reviews material received from the account holder, processes the transaction and performs a third party review for eligibility as a Section 213(d) expense; and
      iii. If the PSP determines that the expense is a qualified expense under 213(d), the PSP enters the medical expense information into the account administration system, which stores the information (including an electronic copy of the submitted receipts and other supporting documentation) in the claims vault for later use.

6. Distribution Process
   a. For automatic distribution: the account administration system releases the requested funds to the custodial account manager for processing.
   b. Since the distribution is based on a credit card swipe, the related funds are sent to the issuing bank associated with the credit card to be applied to the account associated with the credit card.
   Note: For deferred distribution: the account holder pays the credit card's issuing bank upon receipt of the account holder's monthly statement. The documentation associated with the claim remains in the claims vault and the HSA funds remain in the HSA for later distribution.

Exemplary End-of-Year-Account Settlement

As noted above, in various embodiments of the invention, claims (and related supporting information) are entered into the account administration system throughout the year via: (1) manual entry by the account holder; (2) automatic entry via a debit card or credit card transaction; (3) entry by the PSP; or (4) automatic entry via a credit card reimbursement request.

Distributions may be requested from the HSA throughout the year. As noted above, some of these distributions may be classified as qualified distributions, while others may be classified as non-qualified distributions.

As noted above, in one embodiment of the invention, the claims management system is configured to allow the account holder to associate qualified claim documentation records from the system's claims vault with distributions made for non-qualified purchases. This method allows for a distribution of HSA funds at any time throughout the year and for that distribution to be later classified as a tax-free distribution by later associating the distribution with one or more qualified claim documentation records that are substantiated by documentation of a transaction conducted after the distribution was made.

HSA Investment Sub-Accounts

As discussed above, in various embodiments of the invention, the account holder has an HSA established at one or more custodians (e.g., custodians participating in the HSA-Today™ program). In certain embodiments of the invention, the account administration system is configured to allow individuals to invest funds from their HSA in various financial instruments such as mutual funds, money market accounts, or CD's. In one embodiment of the invention, this is done by allowing the account holder to invest money from their HSA in one or more investment sub-accounts (such as money market accounts or mutual funds). Each of these investment sub-accounts may be maintained by the custodian that administers the HSA, or by another financial institution (e.g., another custodian).

In one embodiment of the invention, the custodial account manager provides investment options that have been selected by a registered investment advisor to ensure diversity and security to the best of their ability. There may be various types of funds classified such as Conservative, High Growth, Bond, and International funds. Each fund typically has a fully disclosed collection of individual stocks or other investment vehicles. The account holder may choose to invest money from their HSA in these various funds (which, as noted above, may be set up as sub-accounts within the HSA). In various embodiments of the invention, investment of HSA funds may be "self-directed", "advisor assisted", or "advisor directed".

In a self-directed model according to one embodiment of the invention, the account holder uses the account administration system to send instructions to the custodial account manager to move a specific portion of the established HSA to specified sub-accounts that are selected based solely (or at least primarily) on the discretion of the account holder. In various embodiments, if a distribution is later requested for an amount in excess of the remaining balance of HSA's transaction account, the account administration system sends a message to the account holder indicating that they must move money (e.g., via a request to the custodial account manager) from an appropriate investment sub-account back to the HSA's transaction account. The distribution may then be completed, for example, as discussed above.

In an advisor-assisted model according to various embodiments of the invention, the account holder sends instructions to the custodial account manager to move a specific portion of the account holder's HSA to the selected investment sub-accounts based on the expert advice of a registered investment advisor. The RIA may be compensated for their time by directly billing the account holder. Alternatively, the RIA may be compensated by the HSA administration program (e.g., the HSAToday™ program).

In an advisor-directed model according to various embodiments of the invention, the RIA would typically send instructions to the custodial account manager to move a specific potion of the HSA to investment accounts selected by the RIA. The RIA would act on behalf of the account holder but would be allowed to move funds in and out of various investment sub-accounts without prior approval from the account holder. The RIA may be compensated, for example, as a percentage of the net gain of the various accounts.

Since, in various embodiments of the invention, the accounting for the HSA is actually done by the custodial account manager, in certain embodiments, the balances of all accounts associated with the account holders' HSA (e.g., the HSA transaction account and the various investment sub-accounts) can be combined to form a single HSA account balance. In certain embodiments, the custodial account manager may issue a consolidated report (which is preferably generated by the account administration system) showing the account holder's comprehensive HSA account balance. In certain embodiments, the account administration system may be configured to generate end-of-year tax documents such as the tax forms 1099 and 5498.

Exemplary Graphical User Interface Screens

As will be understood in view of the discussion above, various graphical user interface (GUI) screens may be used to facilitate communication between the system and one or more users of the system. Examples of such GUI screens are described in detail below. While these screens are shown within an Internet-based implementation of the system, similar screens (or screens of a different format) may be used within other embodiments of the invention.

An exemplary HSA account activity screen is shown in FIG. 9. As may be understood from this figure, this screen may display various types of information related to an HSA account. For example, this screen may display: (1) the beginning balance of the HSA account; (2) the total credits associated with the account; (3) the total debits associated with the account; and/or (4) the account's current balance.

FIG. 10 depicts a claims vault summary screen according to a particular embodiment of the invention. As may be understood from this figure, this screen may display, for example: (1) the total value of receipts submitted for "storage" within the claims vault for later use in supporting disbursements from a particular HSA account; (2) the total value of submitted receipts that have been determined to be unqualified for reimbursement from the HSA account; (3) the total value of receipts that have been submitted in conjunction with the HSA account and that are awaiting certification; (4) the total value of submitted receipts that have been determined to be qualified for reimbursement from the HSA account; (5) the total amount of disbursements that have been made from the HSA account (which is indicated, in FIG. 10, as the "Receipt Value Used"); and/or (6) the value of unused receipts remaining in the claims vault.

FIG. 11 shows an exemplary claims vault entry screen. As may be understood from this figure, this screen provides the user with the option of: (1) entering expense information from a particular receipt into the system for storage within the claims vault; (2) withdrawing money from the user's HSA account; or (3) returning to the main menu. In one embodiment, in response to the user indicating that they would like to enter expense information from a particular receipt into the system, the system proceeds to a claims vault receipt entry screen, an example of which is shown in FIG. 12.

As may be understood from FIG. 12, in various embodiments, the claims vault receipt entry screen allows users to enter information regarding a particular expenditure into the system (e.g., an expenditure that is qualified for reimbursement from the user's HSA account). Such information may include, for example: (1) a reference number for the expenditure; (2) the date that related health services were received; (3) the name of the patient who received the health services; (4) the type of health services received by the patient; (5) the provider of the health services; and/or (6) the account holder's out-of-pocket cost for the services. In various embodiments, the screen may also provide the user with the option to either: (1) self-attest that the expense is qualified for reimbursement from the user's HSA; or (2) request that a Plan Service Provider determine whether the expense qualifies for reimbursement from the user's HSA and, if so, to certify the expense as HSA-qualified.

In various embodiments, in response to the user self-attesting that an expense is qualified for reimbursement from the user's HSA, the expense information is saved into the claims vault along with an indication that the expense has been self-attested by the user. Alternatively, if the user has requested that a Plan Service Provider certify the expense as HSA qualified, the system saves the information for later review by a PSP. If the PSP later certifies the expense as HSA-qualified, the system then stores the expense information into the claims vault along with an indication that the expense has been certified by a PSP as being an HSA-qualified expense.

FIGS. 13 and 14 show upper and lower portions of an exemplary claims vault history screen. As may be understood from FIG. 13, in various embodiments, the claims vault history screen may include summary information for each set of claim receipt information that is stored within the claim vault. This summary information may indicate, for example, the provider of the service rendered, the service rendered, the amount paid by the account holder for the service, and/or an indication as to whether the claim receipt: (1) is awaiting certification; (2) has been certified by a PSP as being qualified for reimbursement from the user's HSA; or (3) was self-attested by the user as being qualified for reimbursement from the user's HSA.

As may be understood from FIG. 14, in various embodiments, the Claims Vault history screen may further include summary information for each request for a withdrawal from the user's HSA account. This summary information may indicate, for example, the date that the request was made, the amount of the request, the reason for the request, the amount of the request that was determined to be ineligible for reimbursement from the HSA, and the amount of any payment that was made in response to the request.

FIG. 15 depicts an exemplary withdrawal request screen, which may be used to request a withdrawal from the user's HSA. As may be understood from this figure, in various embodiments, this screen may display the cash balance in the user's HSA. In addition, this screen may be configured to allow the user to enter an amount of a new withdrawal request, as well as a requested method of withdrawal (e.g., whether the user would prefer to receive the withdrawal in the form of a check, or an electronic transfer into a particular bank account). The screen may be further configured to allow the user to save the withdrawal request after entering the appropriate information.

FIGS. 16-18 depict various screens that a PSP would use to view and edit requests for reimbursement from a particular HSA. For example, the screen shown in FIG. 16 displays a listing of pending current claim requests for HSA account holder Jane Baker, including the current certification status of each request (e.g., whether certification for the request is complete). In various embodiments, the system is configured to allow a PSP to select a particular claim request for editing and/or certification. This may be done via appropriate GUI screens, such as those shown in FIGS. 17 and 18. As may be understood from these figures, such screens may show detailed information regarding the request (e.g., the requested reimbursement amount, and documentation of an expenditure for which reimbursement is requested from the HSA account). If the PSP determines that the expenditure is qualified for reimbursement from the HSA account, the PSP may use a certification screen (see FIG. 18) to update the status of the claim within the system to "PSP certified" status.

As indicated in the discussion above, the system may also be configured to facilitate the investment of funds from a particular HSA account in various types of assets or investment accounts. In various embodiments, the system is preferably configured to display a summary of the assets in which funds from the HSA are invested. This may be done via an appropriate portfolio summary screen, such as the screen shown in FIG. 19.

CONCLUSION

Many modifications and other embodiments of the invention will come to mind to one skilled in the art to which this invention pertains having the benefit of the teachings presented in the foregoing descriptions and the associated drawings. For example, while many aspects of the invention are described above as being implemented within the context of a Health Savings Account, these features may be implemented within the context of other types of accounts.

Accordingly, it should be understood that the invention is not to be limited to the specific embodiments disclosed and that modifications and other embodiments are intended to be included within the scope of the appended exemplary concepts. Although specific terms are employed herein, they are used in a generic and descriptive sense only and not for the purposes of limitation.

We claim:

1. A method of facilitating payments from a benefit reimbursement account, the method comprising:
   receiving a first set of documentation of a first payment that would potentially qualify for reimbursement from a benefit reimbursement account, the benefit reimbursement account being associated with an account holder, wherein the account holder provides the first set of documentation;

using the first set of documentation to verify that the first payment qualifies for reimbursement from the benefit reimbursement account; and after verifying that the first payment qualifies for reimbursement from the benefit reimbursement account:
  (a) storing, in a computer system, an electronic version of the first set of documentation; and
  (b) storing, in the computer system, an indication that the first payment has been verified as being properly reimbursable from the benefit reimbursement account.

2. The method of claim 1, wherein:
(A) the step of verifying that the first payment qualifies for reimbursement from the benefit reimbursement account is done by a plan service provider; and
(B) the plan service provider is a separate entity from the account holder.

3. The method of claim 1, wherein the step of storing the electronic version of the first set of documentation comprises storing the electronic version in a database.

4. The method of claim 1, wherein the step of storing the electronic version of the first set of documentation is done at least partially in response to verifying that the first payment qualifies for reimbursement from the benefit reimbursement account.

5. The method of claim 1, wherein the benefit reimbursement account is funded by a third party.

6. The method of claim 1, wherein the benefit reimbursement account is a Medicare Set-Aside Account.

7. The method of claim 1, wherein the step of verifying that the first payment qualifies for reimbursement from the benefit reimbursement account is done at least partially in response to receiving the first set of documentation.

8. The method of claim 1, wherein the step of verifying that the first payment qualifies for reimbursement from the benefit reimbursement account comprises determining whether the first payment is a type of payment that is reimbursable from the benefit reimbursement account.

9. The method of claim 1, wherein the step of storing the electronic version of the first set of documentation comprises storing the first set of documentation in the computer system for a period of greater than one year.

10. A computer system for facilitating payments from an account, the account being associated with an account holder, the computer system being adapted for:

facilitating the transmission of a first set of documentation of a first payment that would potentially qualify for reimbursement from the account;

receiving verification that the first payment has been verified as qualifying for reimbursement from the account according to a set of reimbursement rules associated with the account;

storing, in memory, an electronic version of the first set of documentation; and storing, in memory, an indication that the first payment has been verified as being properly reimbursable from the account.

11. The computer system of claim 10, wherein the step of storing the electronic version of the first set of documentation comprises storing the electronic version in a database.

12. The computer system of claim 10, wherein:
the account is a benefit reimbursement account;
the account holder is a first account holder.

13. The method of claim 12, wherein the benefit reimbursement account is a Medicare Set-Aside Account.

14. The computer system of claim 10, wherein:
the step of facilitating the transmission of the first set of documentation comprises receiving an electronic Explanation of Benefits for goods or services provided to the account holder.

15. The computer system of claim 14, wherein the computer system is configured for receiving the Explanation of Benefits electronically from one of the group including an insurance carrier, a pharmacy benefit manager, a health plan third party administrator, and a data integrator.

16. The computer system of claim 10, wherein the computer system is configured to allow the account holder to associate one or more disbursements made from the account with the first set of documentation for reporting purposes.

17. The computer system of claim 10, wherein the computer system is configured to allow the account holder to associate a single disbursement made from the account with a plurality of sets of documentation for reporting purposes.

18. The computer system of claim 10, wherein the computer system is configured to allow the account holder to associate one or more disbursements made from the account with the first set of documentation for reporting purposes.

19. The computer system of claim 10, wherein the computer system is configured to allow the account holder to use a graphical user interface associated with the computer system to associate one or more disbursements made from the account with the first set of documentation for reporting purposes.

* * * * *